(12) United States Patent
Liebmann et al.

(10) Patent No.: US 8,367,803 B2
(45) Date of Patent: Feb. 5, 2013

(54) SYNTHETIC REPETITIVE PROTEINS, THE PRODUCTION AND USE THEREOF

(75) Inventors: Burghard Liebmann, Bensheim (DE); Marcus Fehr, Speyer (DE); Daniel Hümmerich, Frankenthal (DE)

(73) Assignee: BASF SE, Ludwigshafen (DE)

( * ) Notice: Subject to any disclaimer, the term of this patent is extended or adjusted under 35 U.S.C. 154(b) by 294 days.

(21) Appl. No.: 12/664,902

(22) PCT Filed: Jun. 16, 2008

(86) PCT No.: PCT/EP2008/057526
§ 371 (c)(1),
(2), (4) Date: Dec. 16, 2009

(87) PCT Pub. No.: WO2008/155304
PCT Pub. Date: Dec. 24, 2008

(65) Prior Publication Data
US 2010/0216189 A1 Aug. 26, 2010

(30) Foreign Application Priority Data
Jun. 20, 2007 (EP) .................... 07110696

(51) Int. Cl.
C07K 19/00 (2006.01)
C12N 15/11 (2006.01)
C12N 15/62 (2006.01)
C12N 15/63 (2006.01)
C12N 15/70 (2006.01)
(52) U.S. Cl. ............... 530/350; 435/69.1; 435/252.3; 435/252.33; 435/320.1; 536/23.1; 536/23.4
(58) Field of Classification Search ............... None
See application file for complete search history.

(56) References Cited

U.S. PATENT DOCUMENTS

| | | | |
|---|---|---|---|
| 6,271,345 B1 | 8/2001 | Waldmann et al. | |
| 7,754,851 B2* | 7/2010 | Scheibel et al. | 530/300 |
| 7,868,146 B2* | 1/2011 | Scheibel et al. | 530/412 |
| 7,951,908 B2* | 5/2011 | Scheibel et al. | 530/300 |
| 8,030,024 B2* | 10/2011 | Scheibel et al. | 435/69.1 |
| 8,034,897 B1* | 10/2011 | Scheibel et al. | 530/300 |
| 8,097,583 B2* | 1/2012 | Scheibel et al. | 514/21.2 |
| 2007/0136825 A1* | 6/2007 | Frommer et al. | 800/3 |
| 2007/0214520 A1* | 9/2007 | Scheibel et al. | 800/288 |
| 2009/0098076 A1* | 4/2009 | Barg et al. | 424/70.1 |
| 2009/0099075 A1* | 4/2009 | Barg et al. | 514/12 |
| 2009/0123967 A1* | 5/2009 | Scheibel | 435/69.1 |
| 2009/0137781 A1* | 5/2009 | Scheibel et al. | 530/353 |
| 2009/0156485 A1* | 6/2009 | Barg et al. | 514/12 |
| 2009/0162896 A1* | 6/2009 | Scheibel | 435/69.1 |
| 2009/0263430 A1* | 10/2009 | Scheibel et al. | 424/400 |
| 2010/0015070 A1* | 1/2010 | Bollschweiler et al. | 424/59 |
| 2010/0029553 A1* | 2/2010 | Scheibel | 514/12 |
| 2010/0037329 A1* | 2/2010 | Frommer et al. | 800/13 |
| 2010/0056438 A1* | 3/2010 | Scheibel et al. | 514/12 |
| 2010/0216189 A1* | 8/2010 | Liebmann et al. | 435/69.1 |
| 2010/0278882 A1* | 11/2010 | Liebmann et al. | 424/401 |
| 2010/0278883 A1* | 11/2010 | Liebmann et al. | 424/401 |
| 2010/0298877 A1* | 11/2010 | Scheibel et al. | 606/231 |
| 2010/0310644 A1* | 12/2010 | Liebmann et al. | 424/450 |
| 2011/0129510 A1* | 6/2011 | Liebmann et al. | 424/401 |
| 2011/0136669 A1* | 6/2011 | Liebmann et al. | 504/351 |

FOREIGN PATENT DOCUMENTS

| | | |
|---|---|---|
| WO | WO-98/01406 A1 | 1/1998 |
| WO | WO-2004/073644 A2 | 9/2004 |
| WO | WO-2004/104021 A2 | 12/2004 |
| WO | WO-2004/104042 A1 | 12/2004 |
| WO | WO-2004/104043 A1 | 12/2004 |
| WO | WO-2005/094868 A1 | 10/2005 |
| WO | WO-2007/014755 A1 | 2/2007 |

OTHER PUBLICATIONS

Ardell, et al. "Tentative identification of a resilin gene in Drosophila melanogaster". Insect Biochemistry and Molecular Biology, 2001, vol. 31, pp. 965-970.
Gosline, J. M., et al. "The mechanical design of spider silks: from fibroin sequence to mechanical function". The Journal of Experimental Biology, 1999, vol. 202, pp. 3295-3303.
Huemmerich D., et al. "Primary Structure Elements of Spider Dragline Silks and Their Contribution to Protein Solubility". Biochemistry, 2004, vol. 43, pp. 13604-13612.
Gosline, J.M., et al. "Elastic proteins: biological roles and mechanical properties". Phil. Trans. R. Soc. Lond., B, 2002, vol. 357, pp. 121-132.
Database Uniprot; Accession No. Q9BITO; Jun. 1, 2001; Fibroin 3, XP002496497.

* cited by examiner

Primary Examiner — Manjunath Rao
Assistant Examiner — William W Moore
(74) Attorney, Agent, or Firm — Connolly Bove Lodge & Hutz, LLP

(57) ABSTRACT

A repetitive protein having repetition units comprising the consensus sequence (I)

$$X_1\ X_2\ X_3\ X_4\ S\ X_5\ X_6\ Y\ G$$

Figure 1:
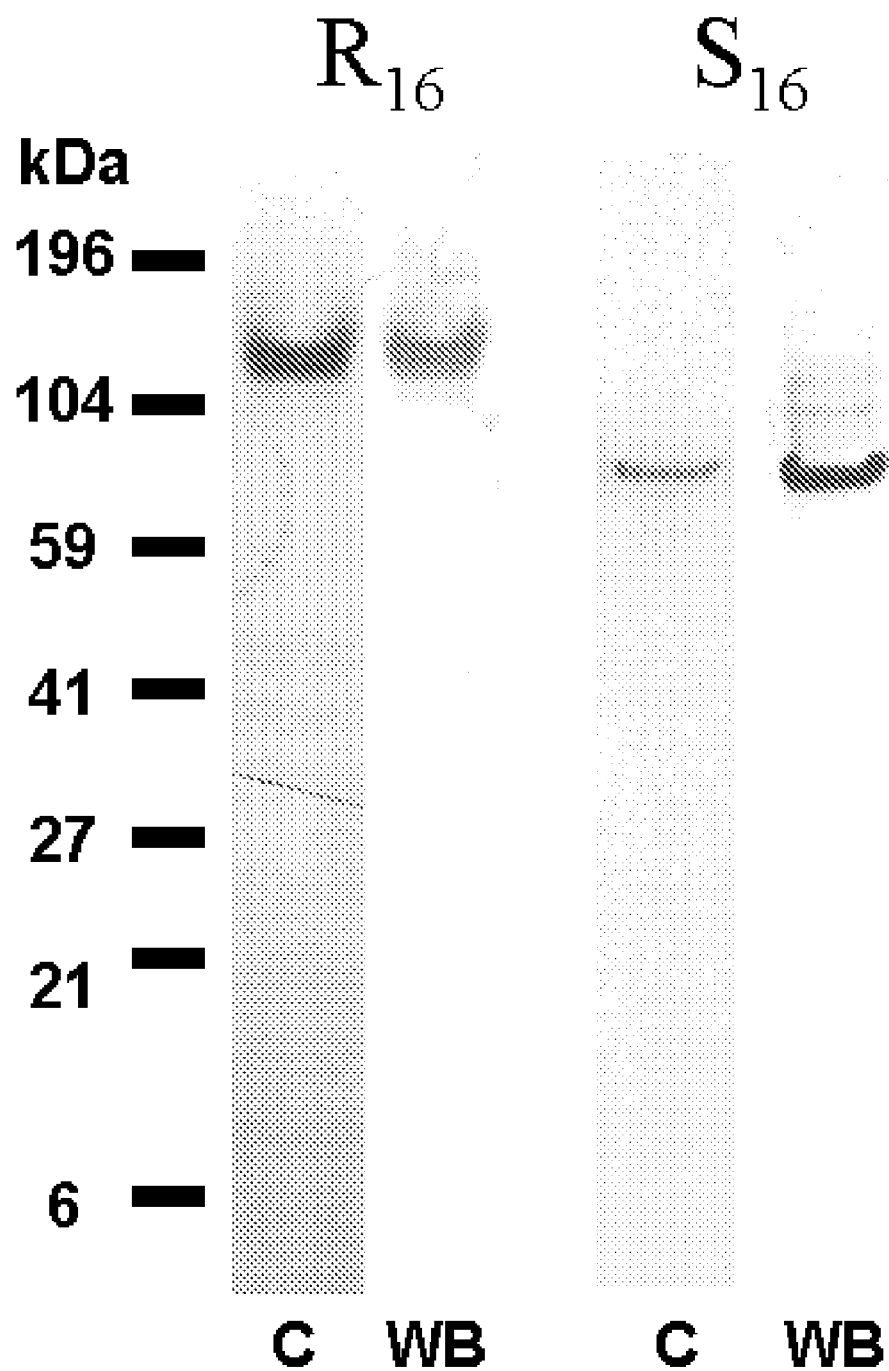

wherein
$X_1$ is G, Y, A or N
$X_2$ is G, L, Q
$X_3$ is R, K, T or P
$X_4$ is P, A, T or S
$X_5$ is D, T or S
$X_6$ is S, Q or T, and
the consensus sequence (II)

$$Z_1\ Z_2\ (Z_3A)_n Z_4\ Z_5\ Z_6$$

wherein
$Z_1$ is S, Q, N, T or G
$Z_2$ is not an amino acid or A
$Z_3$ is A or G
$Z_4$ is not an amino acid, A or S
$Z_5$ is G, S, Q, N or T
$Z_6$ is G, P, S, Q, N or T
n is a natural whole number, wherein $2 \leq n \leq 12$.

7 Claims, 8 Drawing Sheets

SYNTHETIC REPETITIVE PROTEINS, THE PRODUCTION AND USE THEREOF

RELATED APPLICATIONS

This application is a national stage application under 35 U.S.C. §371 of PCT/EP2008/057526, filed Jun. 16, 2008, which claims benefit of European application 07110696.7, filed Jun. 20, 2007.

SUBMISSION OF SEQUENCE LISTING

The Sequence Listing associated with this application is filed in electronic format via EFS-Web and hereby is incorporated by reference into the specification in its entirety. The name of the text file containing the Sequence Listing is Sequence Listing 12810_00967_ST25. The size of the text file is 28.3 kb; the text file was created on Dec. 15, 2009.

The present invention relates to novel synthetic, repetitive proteins, and to the production and use thereof.

BACKGROUND OF THE INVENTION

WO 2004/104043 describes synthetic bioelastomers derived from the repetitive sequence of resilin, and the use thereof. Hybrid molecules composed of resilin sequences and of sequences from other proteins such as spider silk, for example, are likewise described.

The properties of different repetitive proteins are described in the literature. For example, resilins are known for their good elastic properties and the high proportion of elastically stored energy (resilience) (Gosline et al., Philosophical Transactions of the Royal Society of London—Series B: Biological Science, 357(1418): 121:32, 2002). Spider silks are known inter alfa for their high tensile strength and toughness (Gosline et al.; J Exp Biol.; 202(Pt 23): 3295-303 (1999)).

DESCRIPTION OF THE INVENTION

The invention relates to a repetitive protein having repetition units comprising the consensus sequence (I)

$$X_1\ X_2\ X_3\ X_4\ S\ X_5\ X_6\ Y\ G$$

wherein
$X_1$ is G, Y, A or N
$X_2$ is G, L, Q
$X_3$ is R, K, T or P
$X_4$ is P, A, T or S
$X_5$ is D, T or S
$X_6$ is S, Q or T, and
the consensus sequence (II)

$$Z_1\ Z_2\ (Z_3 A)_n Z_4\ Z_5\ Z_6$$

wherein
$Z_1$ is S, Q, N, T or G
$Z_2$ is not an amino acid or A
$Z_3$ is A or G
$Z_4$ is not an amino acid, A or S
$Z_5$ is G, S, Q, N or T
$Z_6$ is G, P, S, Q, N or T
n is a natural whole number, wherein $2 \leq n \leq 12$.

Repetitive proteins according to the present invention are characterized by at least 60%, preferably at least 80%, of their amino acid sequence consisting of repetition units.

A repetition unit is an amino acid sequence of from 7-100, preferably 12-60, and particularly preferably 15-40, amino acids in length, which occurs by way of an identical sequence or a variation with 70%, preferably at least 80%, and particularly preferably at least 90%, identity several times in a protein. Repetitive proteins according to the present invention may comprise identical copies or variations of a single or a plurality of different amino acid sequences.

The repetition units may be connected through linkers comprising preferably from 1 to 30 amino acids, particularly preferably from 1 to 20 amino acids. The amino acid sequence of a linker may be derived from other proteins, preferably structural proteins, or may not have any natural model or be completely absent.

Any number of repetition units, preferably 1-100, particularly preferably 10-65, and most preferably 15-35, may be joined together.

The term consensus sequence, as used herein, refers to an amino acid sequence comprising amino acids frequently occurring at a particular position, wherein other amino acids are not defined in any detail but are replaced with the placeholder X in place of the normally used one letter code for amino acids.

The one letter code for amino acids used herein is known to the skilled worker.

In one embodiment, the ratio of the number of consensus sequences (I) to the number of consensus sequences (II) in 60%, preferably at least 80%, of the repetition units of the repetitive protein is less than five and greater than two.

In one embodiment, the ratio of the number of consensus sequences (I) to the number of consensus sequences (II) in 60%, preferably at least 80%, of the repetition units of the repetitive protein is two or less than two and greater than one, preferably two.

In one embodiment, the ratio of the number of consensus sequences (I) to the number of consensus sequences (II) in 60%, preferably at least 80%, of the repetition units of the repetitive protein is one or less than one, preferably one.

In one development, 60%, preferably at least 80%, of the repetition units of the repetitive protein comprise the subsequence GGRPSDTYG (residues 42-50 of SEQ ID NO: 2) or GGRPSSSYG (residues 47-55 of SEQ ID NO: 4).

In one embodiment, at least 60%, preferably at least 80%, of the repetition units of the proteins according to the invention comprise the sequence motifs $A_n$ or $(GA)_m$ wherein A = alanine, G=glycine, n=2-12, m=2-10, preferably n=5-10, m=4-8 and particularly preferably n =7-9, m =6-7.

In a further embodiment, the repetitive proteins comprise the repetition units PGSSAAAAAAAASG-PGQGQGQGQGQGGRPSDTYG (residues 51-84 of SEQ ID NO: 2) or SAAAAAAAAGPGGGNGGRPSDTYGA-PGGGNGGRPSSSYG (residues 95-133 of SEQ ID NO: 4).

In a further embodiment, the repetitive protein according to the invention comprises aminoterminally or carboxyterminally a peptide sequence of 4-30, and particularly preferably 5-15, amino acids in length, which is used for detecting said protein by means of immunoblotting or for purifying said protein by affinity chromatography. Nonlimiting examples of such peptide sequences are 6 xHis tag (HHHHHH) (SEQ ID NO: 5), T7 tag (MASMTGGQQMG) (SEQ ID NO: 6), S tag (KETAAAKFERQHMDS) (SEQ ID NO: 7), c-Myc tag (EQKLISEEDL) (SEQ ID NO: 8), Strep tag (WSHPQFEK) (SEQ ID NO: 9) and HA tag (YPYDVPDYA) (SEQ ID NO: 10) (Terpe; Appl Microbial Biotechnol; 60(5): 523-33 (2003)). Amino acid sequences may be inserted between the protein according to the invention and the additional peptide sequence, which enable said peptide sequence to be removed chemically or enzymatically.

In a further development, the amino acid sequence of the repetitive protein corresponds to SEQ ID NO 2 or parts of this sequence.

In a further development, the amino acid sequence of the repetitive protein corresponds to SEQ ID NO 4 or parts of this sequence.

The repetitive proteins according to the invention have surprising new properties. These new properties concern, for example, the stability of aqueous protein solutions and the assembling properties. Moreover, the novel repetitive proteins were found to confer advantageous properties to cosmetic or dermatological compositions, in particular to be able to improve the hydrating or softening action. The novel repetitive proteins furthermore behave like good film formers and in particular have a low surface density.

The present invention therefore also relates to the use of monomeric or assembled novel repetitive proteins in cosmetics, in human and animal nutrition, for the formulation of substances, for refining paper, leather and textiles, and for the coating of surfaces.

Repetitive proteins can be produced by expressing natural gene sequences which have been molecular-biologically modified in order to obtain the structure according to the invention. Methods of isolating and modifying natural gene sequences are known to the skilled worker.

Repetitive proteins are preferably produced by expressing synthetically produced gene sequences. One possibility of producing synthetic gene sequences is described in Huemmerich et al., Biochemistry. 43(42):13604-12, (2004).

The invention further relates to nucleic acid sequences coding for the proteins described above. Preferred nucleic acid sequences are SEQ ID NO 1 and SEQ ID NO 3.

The invention further relates to expression vectors comprising the nucleic acid sequences mentioned above. The term expression vector generally refers to a genetic element which can be introduced into a host organism and there enables a desired nucleotide sequence to be expressed. Examples of expression vectors are plasmids, phages or viruses. Expression vectors preferably comprise regulatory elements such as promoters or enhancers, the corresponding coding nucleotide sequence, transcription initiators and transcription terminators, and elements enabling the vector to be multiplied.

The expression systems for proteins are well known and have been described in Sambrook et al.: Molecular cloning: A Laboratory Manual; $3^{rd}$ Ed. Cold Spring Harbour Laboratory Press; Cold Spring Harbour (2001).

Nonlimiting examples of prokaryotic expression organisms are *Escherichia coli, Bacillus subtilis, Bacillus megaterium, Corynebacterium glutamicum*, and others. Nonlimiting examples of eukaryotic expression organisms are yeasts such as *Saccharomyces cerevisiae, Pichia pastoris*, and others, filamentose fungi such as *Aspergillus niger, Aspergillus oryzae, Aspergillus nidulans, Trichoderma reesei, Acremonium chrysogenum*, and others, mammalian cells such as HeLa-cells, COS cells, CHO cells, and others, insect cells such as Sf9 cells, MEL cells, and others, plants or plant cells such as *Solanum tuberosum, Nicotiana*, and others.

The invention further relates to assembling the repetitive proteins to give protein microbeads, nanofibrils, gels and films.

Protein microbeads can be produced preferably by the process described below:

The repetitive protein is dissolved in a first solvent. Examples of solvents that may be used are aqueous salt solutions. Particularly suitable are highly concentrated salt solutions with a concentration of more than 2, in particular more than 4, and particularly preferably more than 5 molar, whose ions have more pronounced chaotropic properties than sodium ions and chloride ions. An example of this kind of salt solution is 6 M guanidinium thiocyanate or 9 M lithium bromide. Furthermore, organic solvents may be used for dissolving the repetitive proteins. Particularly suitable are fluorinated alcohols or cyclic hydrocarbons. Examples of these are hexafluoroisopropanol and cyclohexane. The protein microbeads may be prepared in the solvents described. Alternatively, this solvent may be replaced with another solvent, for example low concentration salt solutions (c<0.5 M) by means of dialysis or dilution. The final concentration of the dissolved protein should be between 0.1-100 mg/ml. The temperature at which the process is carried out is usually 0-80, preferably 5-50, and particularly preferably 10-40° C.

When using aqueous solutions, a buffer, preferably in the range of pH 4-10, particularly preferably 5 to 9, very particularly preferably 6 to 8.5, may additionally be added to said solutions.

Addition of an additive induces phase separation, producing a protein-rich phase emulsified in the mixture of solvent and additive. Owing to surface effects, emulsified protein-rich droplets acquire a round shape. The average diameter of the protein microbeads can be set to values of from 0.1 μm to 50 μm as a result of the selection of solvent, additive and protein concentration.

Additives which may be used are any substances which firstly are miscible with the first solvent and secondly induce the formation of a protein-rich phase. If the microbeads are formed in organic solvents, then organic substances having a lower polarity than the solvent, for example toluene, are suitable for this. In aqueous solutions, salts, whose ions have more pronounced cosmotropic properties than sodium ions and chloride ions (e.g. ammonium sulfate; potassium phosphate), may be used as additives. The final concentration of the additive should be between 1% and 50% by weight, based on the protein solution, depending on the type of additive.

The protein-rich droplets are fixed by curing, with the round shape being retained. Fixing here is based on the formation of strong intermolecular interactions. The type of interactions may be noncovalent, for example due to the formation of intermolecular β-sheet crystals, or covalent, for example due to chemical crosslinking. Curing may be carried out by the additive and/or by adding another suitable substance. Curing takes place at temperatures of between 0 and 80° C., preferably between 5 and 60° C.

Said further substance may be a chemical crosslinker. A chemical crosslinker here means a molecule in which at least two chemically reactive groups are connected to one another via a linker. Examples thereof are sulfhydryl-reactive groups (e.g. maleimides, pydridyl disulfides, α-haloacetyls, vinyl sulfones, sulfato alkyl sulfones (preferably sulfato ethyl sulfones), amine-reactive groups (e.g. succinimidyl esters, carbodiimides, hydroxymethyl, phosphine, imidoesters, PFP esters, aldehydes, isothiocyanates, etc.), carboxy-reactive groups (e.g. amines, etc.), hydroxyl-reactive groups (e.g. isocyanates, etc.), unselective groups (e.g. aryl azides, etc.), and photo-activatable groups (e.g. perfluorophenyl azide, etc.). These reactive groups may form covalent linkages with amine, thiol, carboxyl or hydroxyl groups present in proteins.

The microbeads may also be cured by using substances forming a covalent linkage between amino acid residues. An example of this is a combination of ammonium peroxodisulfate and tris(2,2'-bipyridyl)dichlororuthenium(II), which mediate the formation of dityrosines under the influence of visible light.

The stabilized microbeads are washed with a suitable further solvent, for example water, and then dried by processes familiar to the skilled worker, for example by lyophilization or spray drying. The successful bead formation is checked with the aid of scanning electron microscopy.

The process for producing microbeads allows hydrophobic active compounds to be enclosed and thereby formulated into the microbeads. This process comprises two steps. In the first step, the hydrophobic active compound and the repetitive protein are dissolved in a shared phase. For this purpose, the active compound and the protein may be dissolved directly by a solvent or a solvent mixture. Alternatively, the active compound and the protein can first be dissolved in different solvents, and the solvents can thereafter be mixed with one another, again producing a shared phase. The shared phase may be a molecularly disperse phase or a colloidally disperse phase.

Dissolving the hydrophobic active compound and the protein in various solvents and subsequently mixing the two solutions is particularly advantageous if the hydrophobic active compound and the protein cannot be dissolved in a shared solvent or solvent mixture. In this manner, it is also possible to prepare by this procedure colloidally disperse solutions of hydrophobic active compounds by diluting the active compound which has been dissolved in a suitable solvent into a different solvent in which said active compound is insoluble.

Since proteins usually have good solubility in water, preference is given to working with aqueous solutions and mixtures of water and water-miscible, organic solvents. Examples of suitable, water-miscible solvents are alcohols such as methanol, ethanol and isopropanol, fluorinated alcohols such as hexafluoroisopropanol and trifluoroethanol, alkanones such as acetone, or else sulfoxides such as, for example, dimethyl sulfoxide, or formamides such as dimethylformamide, or other organic solvents such as, for example, tetrahydrofuran and acetonitrile or N-methyl-2-pyrrolidone. In general, it is possible to work with any solvents and solvent mixtures in which the proteins according to the invention can be dissolved. Examples of suitable solvents are fluorinated alcohols such as, for example, hexafluoroisopropanol or trifluoroethanol, ionic liquids such as, for example, EMIM acetate, aqueous solutions of chaotropic salts such as, for example, urea, guanidiunium hydrochloride and guanidinium thiocyanate, or organic acids such as, for example, formic acid, and also mixtures of these solvents with other organic solvents. Examples of solvents which can be mixed with the solvents for the protein are, inter alia, alcohols such as methanol, ethanol and isopropanol, alkanones such as acetone, sulfoxides such as, for example, dimethyl sulfoxide, formamides such as dimethylformamide, haloalkanes such as methylene chloride, or else other organic solvents such as tetrahydrofuran, for example.

In a second step, phase separation with subsequent curing of the microbeads is induced in the shared active compound-protein solution. This process is carried out according to the same principle as described previously for the preparation of pure protein microbeads. During the formation of the microbeads, the hydrophobic active compounds interact with the repetitive proteins according to the invention.

Interactions between the hydrophobic active compound and the protein are based essentially on their hydrophobic properties, although it is also possible for hydrogen bridges, ionic interactions and van der Waals interactions to be involved. The hydrophobic active compound may be bound to the surface, enclosed in the microbeads or else associated in both ways with the microbeads. Binding of the hydrophobic active compound to the microbeads may be determined by way of depletion of dissolved active compound in the assembling mix. The concentration of the active compound may be measured by quantitative analysis of its properties. Thus, for example, binding of light-absorbing active compounds may be analyzed by photometric methods. For this purpose, for example, staining of the microbeads or destaining of the protein- and active compound-depleted phase of the formulation mix is determined by measuring absorption of the colored active compound. The proportion of active compound in the microbeads may also be determined with the aid of these methods.

The active compounds can be released from the microbeads by desorption into suitable solvents, by degradation of the microbeads by proteases, or by dissolving the microbeads by means of suitable solvents. Suitable solvents for desorption are any solvents or solvent mixtures, in which the active compound can be dissolved. Suitable proteases may be specifically added by way of technical proteases to a suspension of protein microbeads or may be present naturally at the desired site of action of the effector molecules, such as, for example, proteases of the skin, proteases of the gastrointestinal tract, for example proteases of the stomach or intestine, or proteases released by microorganisms. Solvents capable of dissolving the microbeads are, for example, fluorinated alcohols such as, for example, hexafluoroisopropanol or trifluoroethanol, ionic liquids such as, for example, EMIM acetate, aqueous solutions of chaotropic salts such as, for example, urea, guanidinium hydrochloride and guanidinium thiocyanate, or organic acids such as, for example, formic acid, and also mixtures of these solvents with other organic solvents. The rate and kinetics of the release of the effector molecules may be controlled, for example, via the density of occupation with active compounds and the size of the microbeads or their volume-to-surface ratio.

Under suitable conditions, nanofibrils can be prepared from the repetitive proteins according to the invention. The formation of nanofibrils manifests itself at the macroscopic level by way of a gel-like thickening of an aqueous protein solution at a nanofibril concentration of equal to or higher than 1 mg/ml.

The starting point for assembling protein nanofibrils is an aqueous solution of the repetitive protein with a protein concentration of 0.1-400 mg/ml, preferably 1-100 mg/ml, and particularly preferably 5-20 mg/ml. The aqueous solution may be admixed with a buffer, preferably in the range of pH 4-10, particularly preferably 5 to 9, very particularly preferably 6 to 8.5. The assembling process takes place by itself within a period of several weeks. It may be accelerated by the addition of water-soluble organic solvents which reduce the polarity of the solution. Examples of these are alcohols such as ethanol and methanol. The final concentration of the solvent should be between 1% and 50% by weight, based on the protein solution.

The assembled protein nanofibrils are washed with a suitable solvent, for example water, and subsequently dried by processes familiar to the skilled worker, for example by lyophilization, contact drying or spray drying. Successful formation of fibers is tested with the aid of transmission electron microscopy or scanning force microscopy.

Under suitable conditions, films may be prepared from the repetitive proteins according to the invention. For this purpose, the repetitive protein is dissolved in a first solvent.

Examples of solvents which may be used are aqueous salt solutions. Particularly suitable are highly concentrated salt solutions with a concentration of more than 2, in particular more than 4, and particularly preferably more than 5, molar, whose ions have more pronounced chaotropic properties than sodium ions and chloride ions. An example of such a salt solution is 6 M guanidinium thiocyanate or 9 M lithium bromide. It is furthermore possible to use organic solvents for dissolving the repetitive proteins. Fluorinated alcohols or cyclic hydrocarbons are particularly suitable. Examples thereof are hexafluoroisopropanol and cyclohexane. The films may be prepared in the first solvent described, as long as it does not comprise any nonvolatile substances. Solvents comprising nonvolatile components must be replaced by another solvent that does not comprise any nonvolatile substances, for example by dialysis. Preferred volatile solvents, out of which the films can be formed, are hexafluoroisopropanol, cyclohexane, formic acid and water. The final concentration of the dissolved protein should be between 1-200 mg/ml, preferably between 20-150 mg/ml, and particularly preferably between 50-100 mg/ml. The temperature, at which the process is carried out, is usually 0-80, preferably 5-50, and particularly preferably 10-40° C. The repetitive protein dissolved in the volatile solvent is plated out on a smooth surface. The solvent evaporates at room temperature, leaving the protein film behind.

Freshly prepared protein films are normally water-soluble. The films may be stabilized by incubating them with substances inducing the formation of stable secondary, tertiary and quaternary structures within the film. Examples of such substances are alcohols such as, for example, methanol and ethanol, or solutions of salts, whose ions have more pronounced cosmotropic properties than sodium ions and chloride ions (e.g. ammonium sulfate; potassium phosphate). After the films have been stabilized, they may be washed with suitable solvents such as, for example, alcohols or water and then dried.

The invention further relates to molecules consisting of couplings of a repetitive protein according to the invention and an effector molecule. Effector molecules mean molecules which have a particular, predictable action. They may be either protein-like molecules such as enzymes or else non-proteinogenic molecules such as dyes, light stabilizers, vitamins, provitamins, antioxidants and fatty acids, conditioners or metal ion-comprising compounds.

The effector molecules are connected to the repetitive protein. The connection between the effector molecule and the protein may be both a covalent bond and a connection based on ionic or van der Waals interactions or hydrophobic interactions or hydrogen bonds or adsorption.

The effector molecule may be covalently linked via the side chains of the polypeptide sequence of the repetitive protein, in particular via amino functions or hydroxy functions or carboxylate functions or thiol functions. Preference is given to a linkage via the amino functions of one or more lysine residues, via the carboxylate functions of one or more glutamate or aspartate residues, via the thiol function of one or more cystein residues, or via the N-terminal or C-terminal function of the repetitive protein. It is also possible to add to or insert into the sequence, in addition to the amino acid functions present in the amino acid sequence, amino acids with suitable functions (e.g. cysteins, lysines, aspartates, glutamates), or to substitute such amino acid functions for amino acids of the repetitive protein.

The effector molecules may be linked to the repetitive protein directly, i.e. by way of covalent linkage of two chemical functions already present. This involves linking the above-described chemical functions of the repetitive proteins to reactive groups present in the effector molecules. Examples of such reactive groups are sulfhydryl-reactive groups, for example maleimides, pydridyl disulfides, α-haloacetyls, vinyl sulfones, sulfato alkyl sulfones (preferably sulfato ethyl sulfones), amine-reactive groups (e.g. succinimidyl esters, carbodiimides, hydroxymethyl phosphine, imidoesters, PFP esters, aldehyde, isothiocyanate, etc.), carboxy-reactive groups (e.g. amines, etc.), hydroxyl-reactive groups (e.g. isocyanates, etc.), unselective groups (e.g. aryl azides, etc.), and photoactivatable groups (e.g. perfluorophenyl azide, etc.).

If the reactivity of the functions to be coupled of the repetitive proteins and effectors according to the invention is too low for direct coupling, said functions may be activated by methods familiar to the skilled worker (e.g. activation of carboxyl functions with carbodiimides).

However, linkage may also take place via a "linker", i.e. an at least bifunctional molecule, which binds to the effector molecule with one or more functions and which is linked to the repetitive protein with one or more different functions.

Using such tailored linkers allows the linkage to be precisely matched with the desired effector molecule. Moreover, this enables a plurality of effector molecules to be linked to a repetitive protein in a defined manner.

The linker used depends on the functionality to be coupled. Suitable examples are molecules which couple to a repetitive protein by means of sulfhydryl-reactive groups, for example maleimides, pydridyl disulfides, α-haloacetyls, vinyl sulfones, sulfato alkyl sulfones (preferably sulfato ethyl sulfones), amine-reactive groups (e.g. succinimidyl esters, carbodiimides, hydroxymethyl phosphine, imidoesters, PFP esters, aldehyde, isothiocyanate, etc.), carboxy-reactive groups (e.g. amines, etc.), hydroxyl-reactive groups (e.g. isocyanates, etc.), unselective groups (e.g. aryl azides, etc.) and photoactivatable groups (e.g. perfluorophenyl azide, etc.), and coupled to effector molecules by means of sulfhydryl-reactive groups (e.g. maleimides, pydridyl disulfides, α-haloacetyls, vinyl sulfones, sulfato alkyl sulfones (preferably sulfato ethyl sulfones)

amine-reactive groups (e.g. succinimidyl esters, carbodiimides, hydroxymethyl phosphine, imidoesters, PFP esters, aldehyde, isothiocyanate, etc.)

sugars or oxidized sugar-reactive groups (e.g. hydrazides, etc.)

carboxy-reactive groups (e.g. amines, etc.)

hydroxyl-reactive groups (e.g. isocyanates, etc.)

thymine-reactive groups (e.g. psoralene, etc.)

unselective groups (e.g. aryl azides, etc.)

photo-activatable groups (e.g. perfluorophenyl azide, etc.)

metal-complexing groups (e.g. EDTA, hexaHis, ferritin)

antibodies and antibody fragments (e.g. single-chain antibodies, F(ab) fragments of antibodies, catalytic antibodies).

The chemical functions of a linker may be connected by spacer elements. Spacer elements may be composed, for example, of alkyl chains, ethylene glycol and polyethylene glycols.

Particular preference is given to linker elements and/or spacer elements which have a potential cleavage site for a protease, lipase, esterase, phosphatase, hydrolase, i.e. which are enzymatically cleavable.

Examples of enzymatically cleavable linkers which can be used in the molecules according to the invention, are mentioned, for example, in WO 98/01406, to which in its entirety reference is hereby expressly made.

Particular preference is given to linkers and spacers which are thermo cleavable or photo cleavable. Corresponding chemical structures are known to the skilled worker and are integrated between the effector molecule and repetitive protein moieties of the molecule.

If the effector molecule is composed of a polypeptide sequence, effector and repetitive protein can be linked by way of a "fusion" protein, i.e. a continuous polypeptide sequence is used, which is composed of effector sub-sequences and repetitive protein sub-sequences.

It is also possible to incorporate between effector and repetitive protein also "spacer elements", for example polypeptide sequences which have a potential cleavage site for a protease, lipase, esterase, phosphatase, hydrolase, or oligo- and polypeptide sequences, which enable the fusion protein to be readily purified, for example "His" tags, i.e. oligohistidine residues.

The effector molecules coupled covalently or noncovalently to repetitive proteins may be active in their bound form. Alternatively, the effector molecules coupled to repetitive proteins may also be released from said repetitive proteins, however.

Covalently coupled effector molecules may be released from the repetitive proteins by cleaving specifically introduced cleavable spacers or coupling linkers, which may be, for example, thermo cleavable, photo cleavable or enzymatically cleavable, or else by proteolytic degradation (for example by proteases),

EXPERIMENTAL PART

Example 1

Production of the Repetitive Protein $R_{16}$ (SEQ ID NO:2)

A synthetic gene coding for the repetitive protein $R_{16}$ was multimerized by way of multimerization of a synthetic oligonucleotide R:

ggcccgggttctagcgcggctgcagc-
cgcggcagctgcgtccggcccgggt-
cagggccagggtcagggtcaaggccagggtggccgt ccttctgacacctac
(nucleotides 46-147 of SEQ ID NO: 1) according to the method described in Huemmerich et al.; Biochemistry 43(42): 13604-12, (2004), to give a 16mer and cloned into the expression vector pET21a (Novagen). Expression was carried out in the strain *E. coli* BLR [DE3] (Novagen).

Growth and protein synthesis were carried out in a fed batch process at $pO_2$>20% and pH=6.8.

Medium

| 8 liters | Water |
|---|---|
| 230 g | Yeast extract |
| 150 g | Bacto tryptone |
| 30 g | Glycerol (99%) |
| 20 g | Potassium dihydrogen phosphate ($KH_2PO_4$) |
| 50 g | Ammonium sulfate (($NH_4)_2SO_4$) |
| 10.5 g | Magnesium sulfate heptahydrate ($MgSO_4*7H_2O$) |
| 1.0 g | Calcium chloride dihydrate ($CaCl_2*2 H_2O$) |
| 100 ml | Trace salt solution |
| | Fill to 9.7 liters with water |
| | Adjust pH with 25% strength NaOH to 6.8 |
| 3 ml | Tego KS 911 (antifoam; Goldschmidt product) |
| 1 g | Ampicillin |

Trace Salt Solution:

| 5 liters | Water |
|---|---|
| 200.00 g | Citric acid monohydrate |
| 55.00 g | $ZnSO_4*7H_2O$ |
| 42.50 g | $(NH_4)_2Fe(SO_4)_2*6H_2O$ |
| 15.00 g | $MnSO_4*H_2O$ |
| 4.00 g | $CuSO_4*5H_2O$ |
| 1.25 g | $CoSO_4*7H_2O$ |

Feeding Solution

| 800 g | Water |
|---|---|
| 30 g | Citric acid monohydrate |
| 60 g | Sodium sulfate ($Na_2SO_4$) |
| 4.5 g | $(NH_4)_2Fe(SO_4)_2*6H_2O$ |
| 3400 g | Glycerol 99.5% |

After the glycerol in the base medium had been used up, a constant feed was started at a rate of 100 ml/h.

Protein synthesis was induced by adding 1 mM isopropyl β-D-thiogalactopyranoside, after the bacterial culture had reached an optical density of $OD_{600}$=40. At this time, the temperature of the culture was reduced from 37° C. to 32° C. The cells were harvested for 7 h after induction.

Figure 2:
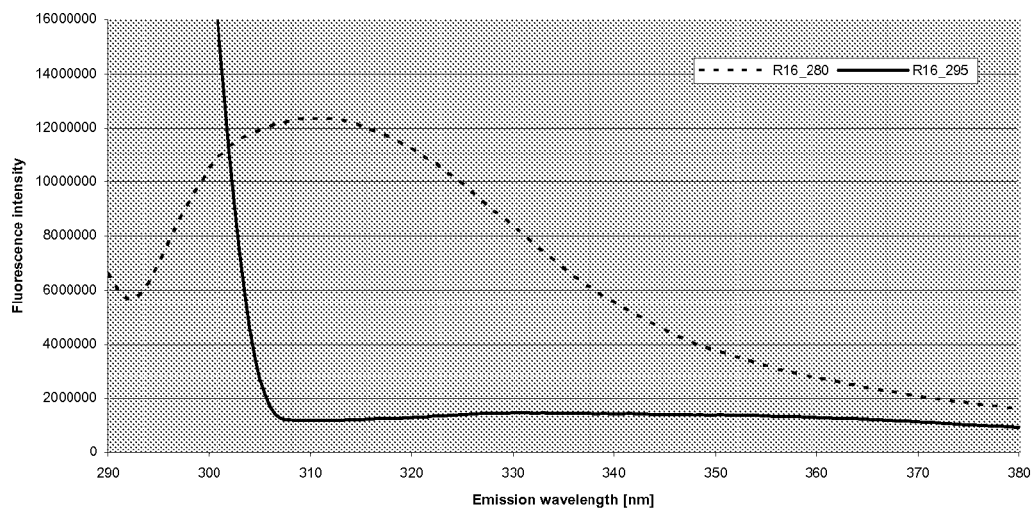
Figure 2:
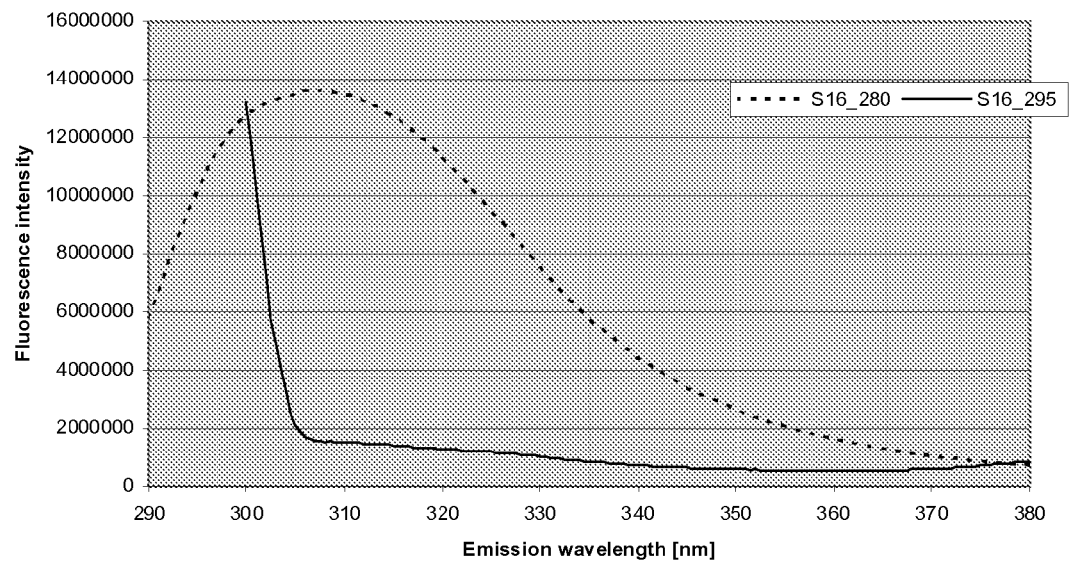

The protein was purified according to the following protocol:

resuspension of the cell pellet in 5 ml of 20 mM MOPS (3-(N-morpholino)propanesulfonic acid) pH 7.0 per gram of wet biomass lysis of the cells in a high pressure homogenizer at 1400 bar centrifugation at 5000×g for 30 min washing of the pellet with 5 ml of 50 mM Tris/HCl pH 8.0; 100 mM NaCl, 0.5 mM ethylenediamine tetraacetate (EDTA), 0.1% Triton X-100 per gram of wet biomass washing of the pellet with 5 ml of 50 mM Tris/HCl pH 8.0; 100 mM NaCl, 0.5 mM ethylenediamine tetraacetate (EDTA) per gram of wet biomass dissolving of the pellet by adding 1.6 g of guanidinium thiocyanate (GdmSCN) per gram of pellet (final concentration: 6 M GdmSCN)

centrifugation at 5000×g for 60 min dialysis of the supernatant against 5 mM potassium phosphate pH 7.0 centrifugation at 5000×g for 30 min precipitation of the protein from the supernatant by adding 1/4 volume of 4 M ammonium sulfate at room temperature for 1 h washing of the pellet with 8 M urea 2× washing of the pellet with water lyophilization the lyophilized protein can be stored at −20° C.

for usage of the protein, the lyophilized protein is taken up in 6 M GdmSCN and dialyzed against 5 mM potassium phosphate pH 7.0 the protein content in solution was determined photometrically ($E_{(280;1mg/ml)}$=0.42)

the purity of the protein was tested by SDS PAGE and Western blot analysis (FIG. 1), and by fluorescence spectroscopy (FIG. 2).

20 g of clean $R_{16}$ protein with a purity of >95% were recovered from a 10 fermentation.

Example 2

Production of the Repetitive Protein $S_{16}$ (SEQ ID NO:4)

A synthetic gene coding for the repetitive protein $S_{16}$ was multimerized by way of multimerization of a synthetic oligonucleotide S:

ggttctgcggctgcagccgcggcagct-
gcgggtccgggcggtggcaacggtggc-
cgtcgtctgacacctacggtgcgccgggtggcg gtaacggtggccgtccttcttc-
ctcttac (nucleotides 45-159 of SEQ ID NO: 3) according to the method described in Huemmerich et al.; Biochemistry 43(42): 13604-12, (2004), to give a 16mer and cloned into the expression vector pET21a (Novagen). Expression was carried out in the strain *E. coli* BLR [DE3] (Novagen).

Growth and protein synthesis were carried out in a fed batch process at $pO_2$>20% and pH=6.8.

Medium

| | | |
|---|---|---|
| 8 liters | Water | |
| 230 g | Yeast extract | |
| 150 g | Bacto tryptone | |
| 30 g | Glycerol (99%) | |
| 20 g | Potassium dihydrogen phosphate ($KH_2PO_4$) | |
| 50 g | Ammonium sulfate (($NH_4)_2SO_4$) | |
| 10.5 g | Magnesium sulfate heptahydrate ($MgSO_4*7H_2O$) | |
| 1.0 g | Calcium chloride dehydrate ($CaCl_2*2H_2O$) | |
| 100 ml | Trace salt solution | |
| | Fill to 9.7 liters with water | |
| | Adjust pH strength with 25% strength NaOH to 6.8 | |
| 3 ml | Tego KS 911 (antifoam; Goldschmidt product) | |
| 1 g | Ampicillin | |

Trace Salt Solution:

| | |
|---|---|
| 5 liters | Water |
| 200.00 g | Citric acid monohydrate |
| 55.00 g | $ZnSO_4*7H_2O$ |
| 42.50 g | $(NH_4)_2Fe(SO_4)_2*6H_2O$ |
| 15.00 g | $MnSO_4*H_2O$ |
| 4.00 g | $CuSO_4*5H_2O$ |
| 1.25 g | $CoSO_4*7H_2O$ |

Feeding Solution

| | |
|---|---|
| 800 g | Water |
| 30 g | Citric acid monohydrate |
| 60 g | Sodium sulfate ($Na_2SO_4$) |
| 4.5 g | $(NH_4)_2Fe(SO_4)_2*6H_2O$ |
| 3400 g | Glycerol 99.5% |

After the glycerol in the base medium had been used up, a constant feed was started at a rate of 100 ml/h.

Protein synthesis was induced by adding 1 mM isopropyl β-D-thiogalactopyranoside, after the bacterial culture had reached an optical density of $OD_{600}$=40. At this time, the temperature of the culture was reduced from 37° C. to 25° C. The cells were harvested for 4 h after induction.

The protein was purified according to the following protocol:
  resuspension of the cell pellet in 5 ml of 20 mM MOPS (3-(N-morpholino)propanesulfonic acid) pH 7.0 per gram of web biomass
  lysis of the cells in a high pressure homogenizer at 1400 bar
  centrifugation at 5000×g for 30 min
  incubation of the supernatant at 80° C. for 20 min
  centrifugation at 5000×g for 30 min
  precipitation of the protein from the supernatant by adding 1 volume of 4 M ammonium sulfate at room temperature for 1 h
  washing of the pellet with 8 M urea
  2× washing of the pellet with water
  lyophilization
  the lyophilized protein can be stored at −20° C.
  for usage of the protein, the ammonium sulfate precipitate is taken up in
  6 M GdmSCN and dialyzed against 5 mM potassium phosphate pH 7.0
  the protein content in solution was determined photometrically ($E_{(280;1mg/ml)}$=0.76)
  the purity of the protein was tested by SDS PAGE and Western blot analysis (FIG. 1), and by fluorescence spectroscopy (FIG. 2).

1.4 g of pure $S_{16}$ protein were recovered from a 10 fermentation.

Example 3

Formation of protein microbeads from repetitive proteins $R_{16}$ and $S_{16}$

Protocol
  dissolving of the lyophilized $R_{16}$ or $S_{16}$ in 6 M guanidinium thiocyanate at a final concentration of 10 mg/ml
  dialysis against 1 M potassium phosphate, pH 7.0 at room temperature
  washing with water
  lyophilization.

Replacing the chaotropic guanidinium thiocyanate with the cosmotropic potassium phosphate induces the formation of $R_{16}$ or $S_{16}$ microbeads. Alternatively, the guanidinium thiocyanate can be removed by dialysis against 5 mM potassium phosphate. Microbead formation is induced by adding ¼ volume of 4 M ammonium sulfate or ½ volume of 1 M potassium phosphate.

Protocol
  dissolving of the lyophilized $R_{16}$ or $S_{16}$ in 6 M guanidinium thiocyanate at a final concentration of 15 mg/ml
  dialysis against 5 mM potassium phosphate pH 7.0 at 4° C.
  removal of precipitate by centrifugation at 10 000×g for 30 min adjusting of the protein concentration to 10 mg/ml
  addition of ¼ volume of 4 M ammonium sulfate or ½ volume of 1 M potassium phosphate
  incubation at room temperature for 1 h
  washing with water
  lyophilization.

Figure 3:
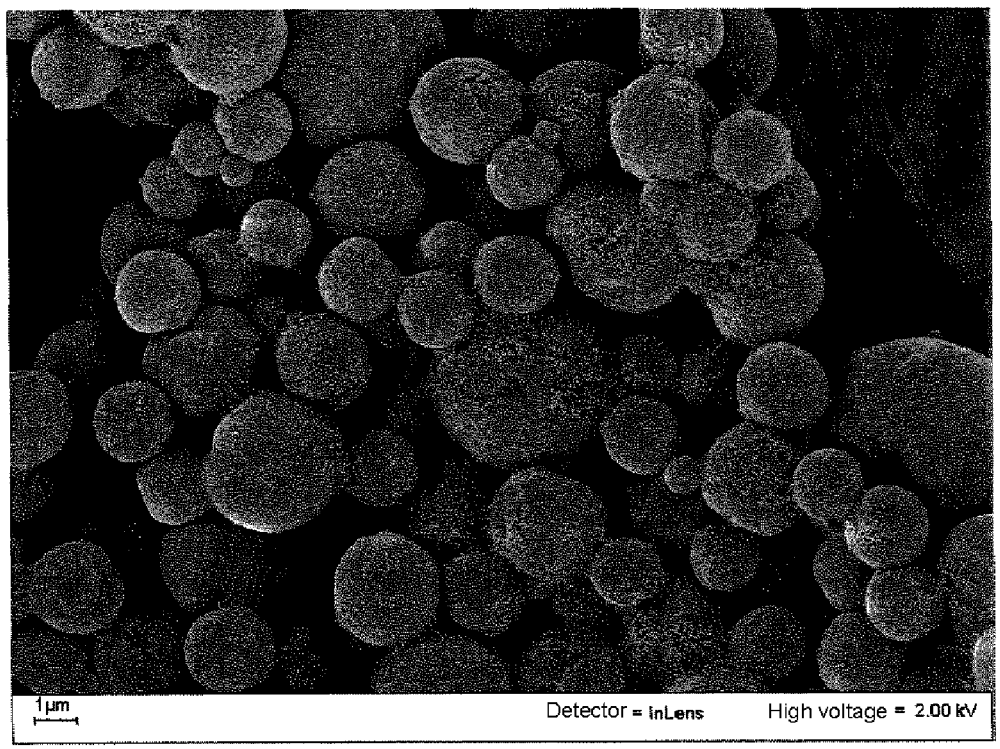

Successful microbead formation is tested with the aid of scanning electron microscopy (FIGS. 3+4).

Example 4

Stabilization of $S_{16}$ Microbeads

The process of $S_{16}$ microbead formation includes phase separation induced by potassium phosphate or ammonium sulfate and subsequent stabilization of the protein-rich phase by forming stable secondary structures. The protein-rich droplets which have not been cured can be distinguished from stabilized microbeads experimentally by their different stability in 4 M urea. The kinetics of the stabilization were examined, Protocol
- preparation of an aqueous 10 mg/ml $S_{16}$-solution in 5 mM potassium phosphate pH 7.0
- precipitation of the $S_{16}$ protein with ¼ volume of 4 M ammonium sulfate at time 0
- removal of a portion of the precipitated protein suspension at time t and mixing thereof with the same volume of 8 M urea
- measurement of the extinction of the sample at 600 nm as a qualitative measure of scattering.

Figure 5:
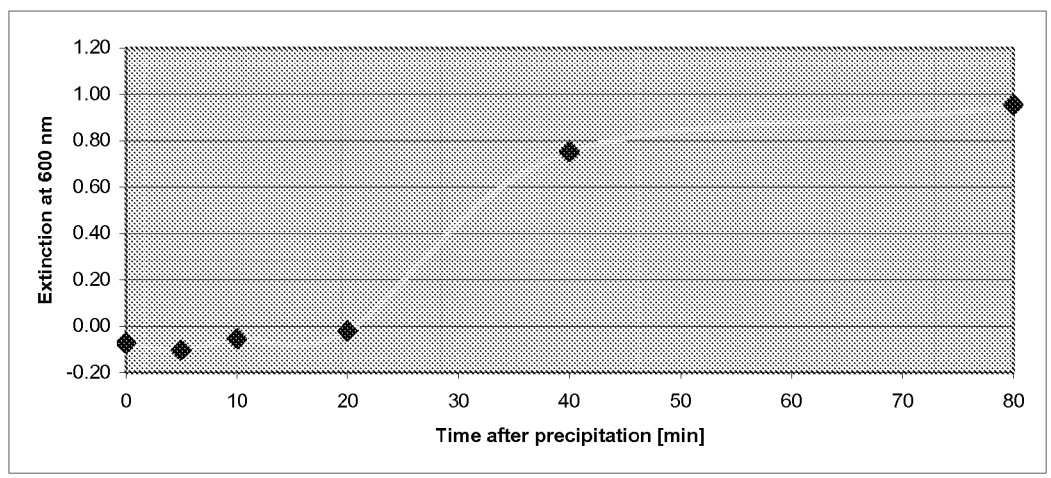

The turbidity of the sample caused by the precipitation can be reversed within 30 min by establishing a concentration of 4 M urea. After 40 min, turbidity remains with this treatment. It may therefore be concluded that a structure has formed in the protein-rich phase during this period, which is stable in 4 M urea (FIG. 5).

Example 5

Packaging of β-carotene in $R_{16}$ and $S_{16}$ microbeads

In order to demonstrate that the $R_{16}$ and $S_{16}$ microbeads are suitable as carriers and formulation excipients for active compounds, β-carotene was packaged by way of example for sparingly water-soluble active compounds into $R_{16}$ and $S_{16}$ microbeads.

For this purpose, 500 μl of a solution of 10 mg/ml $R_{16}$ or $S_{ib}$ in 5 mM potassium phosphate (pH 8.0) were mixed with 50 μl of a solution of 0.9 mg/ml n-carotene in 10% tetrahydrofuran (THF) and 90% N-methyl-2-pyrrolidone (NMP). Thereafter, the formation of microbeads was induced by adding 275 μl of 4 M ammonium sulfate solution.

Figure 6:
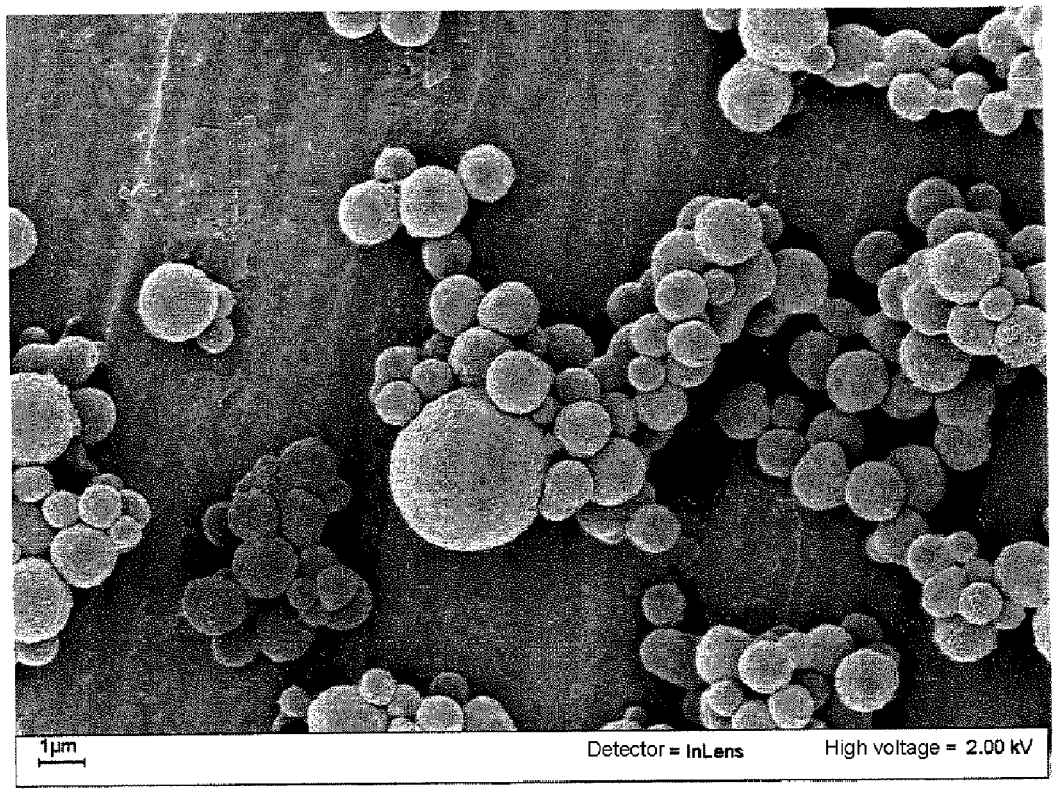

During the formation of $R_{16}$ and $S_{16}$ microbeads, the β-carotene was removed from the solution. The microbeads which have been removed by centrifugation appeared yellow-orange. The microbeads were washed with water, during which process the β-carotene remained associated with the microbeads, and then lyophilized. After lyophilization the loaded $R_{16}$ or $S_{16}$ microbeads were analyzed by scanning electron microscopy (FIGS. 6+7). In the electron-microscopic image, the loaded microbeads (FIGS. 6+7) showed a very similar morphology to the unloaded microbeads (FIGS. 3+4), thereby making clear that the microbeads and the 8-carotene form a shared solid phase.

Example 6

Water absorption by $R_{16}$ Microbeads

Microbeads of repetitive proteins can absorb water from the air and release it and can therefore serve as moisture-regulating substance, for example in cosmetic applications.

Figure 8:
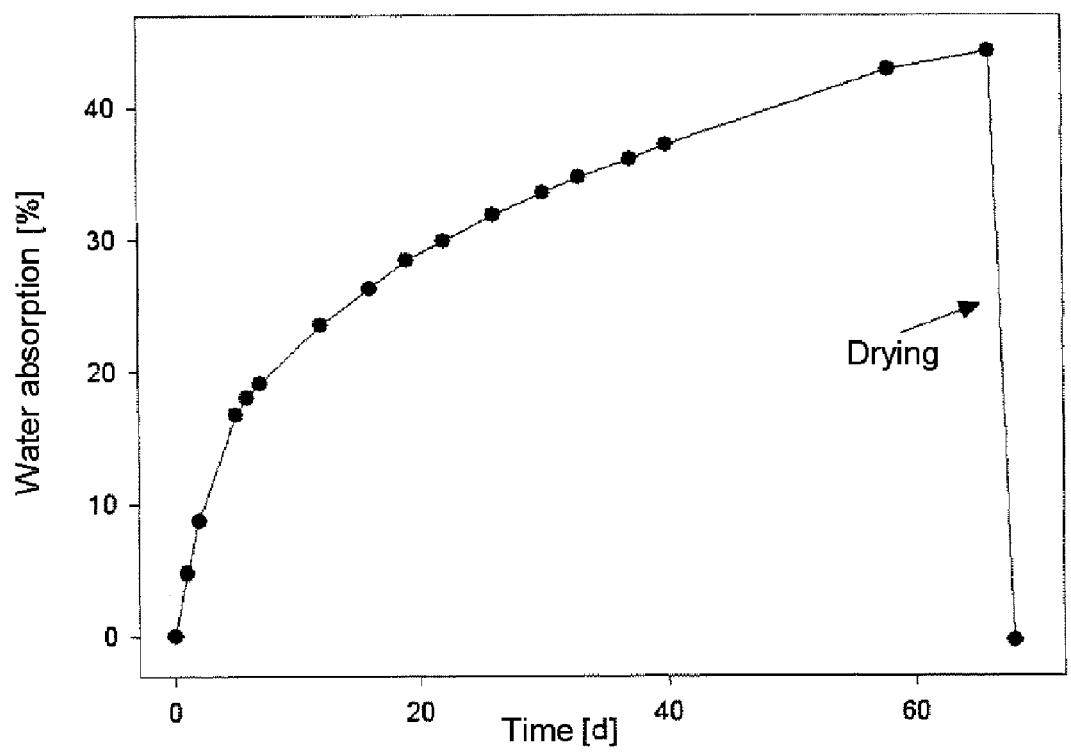

In order to demonstrate this, 0.4 g of $R_{16}$ microbeads which had been stored previously at −20° C. were dried under vacuum for 16 h and the dry weight was determined. Subsequent storage at room temperature and 100% humidity resulted in a slow weight increase of 44% within 66 days (FIG. 8). Removed drying in vacuo reestablished the original dry weight.

Example 7

Gel formation of $R_{16}$ and $S_{16}$

Protocol:
- dissolving of the lyophilized $R_{16}$ or $S_{16}$ in 6M guanidinium thiocyanate at a final concentration of 20 mg/ml
- dialysis against 5 mM potassium phosphate pH 7.0 at 4° C.
- removal of precipitate by centrifugation at 10 000×g for 30 min
- preparation of a solution containing 2.5 mM potassium phosphate pH 7.0, 10 mg/ml $R_{16}$ or $S_{16}$ protein and 40% v/v ethanol
- incubation at room temperature.

The solution attains a gel-like, turbid state within 4-5 days.

Example 8

Film formation of $R_{16}$ and $S_{16}$ is

Protocol
- dissolving of the lyophilized $R_{16}$ or $S_{16}$ in hexafluoroisopropanol at a final concentration of 100 mg/ml
- plating out of 300 μl on a smooth polystyrene surface
- evaporation of the hexafluoroisopropanol at room temperature
- overlaying of the protein film with 1 M potassium phosphate pH 7.0 for 5 min
- 2× washing with water
- drying in air.

This treatment results in transparent, water-insoluble protein films. Dry films of $R_{16}$ are brittle, whereas films of $S_{16}$ have flexible properties.

LIST OF FIGURES

FIG. 1. Analysis of the purified proteins $R_{16}$ and $S_{16}$. An aqueous solution of the proteins was prepared and fractionated electrophoretically on a polyacrylamide gel. The proteins were detected by staining with the dye Coomassie Brilliant Blue (C) or by immunoblotting with an antibody which specifically binds to the T7 peptide tag which is attached to both proteins aminoterminally (WB).

FIG. 2. Purification analysis of purified $R_{16}$ and 516 by means of fluorescence spectroscopy. $R_{16}$ and $S_{16}$ do not comprise the amino acid tryptophan, while tyrosines are present. In contrast, tryptophan is present with an average frequency of 1.5% in E. Coli proteins. Fluorescence spectroscopy can selectively detect the presence of tryptophans in a protein sample and therefore contaminations in $R_{16}$ or $S_{16}$ preparations. While both tyrosines and tryptophans are excited by light of a wavelength of 280 nm (blue), light of 295 nm (magenta) exclusively excites tryptophan. The $R_{16}$ and $S_{16}$ samples exhibit a tyrosine-typical fluorescence, while no indications of the presence of tryptophan are detectable, indicating the high purity of the protein samples.

FIG. 3. $R_{16}$ microbeads. The microbeads were obtained by dialysis of a 10 mg/ml $R_{16}$ solution in 6 M GdmSCN against a 1 M potassium phosphate solution pH 7.0 and analyzed by means of scanning electron microscopy.

Figure 4:
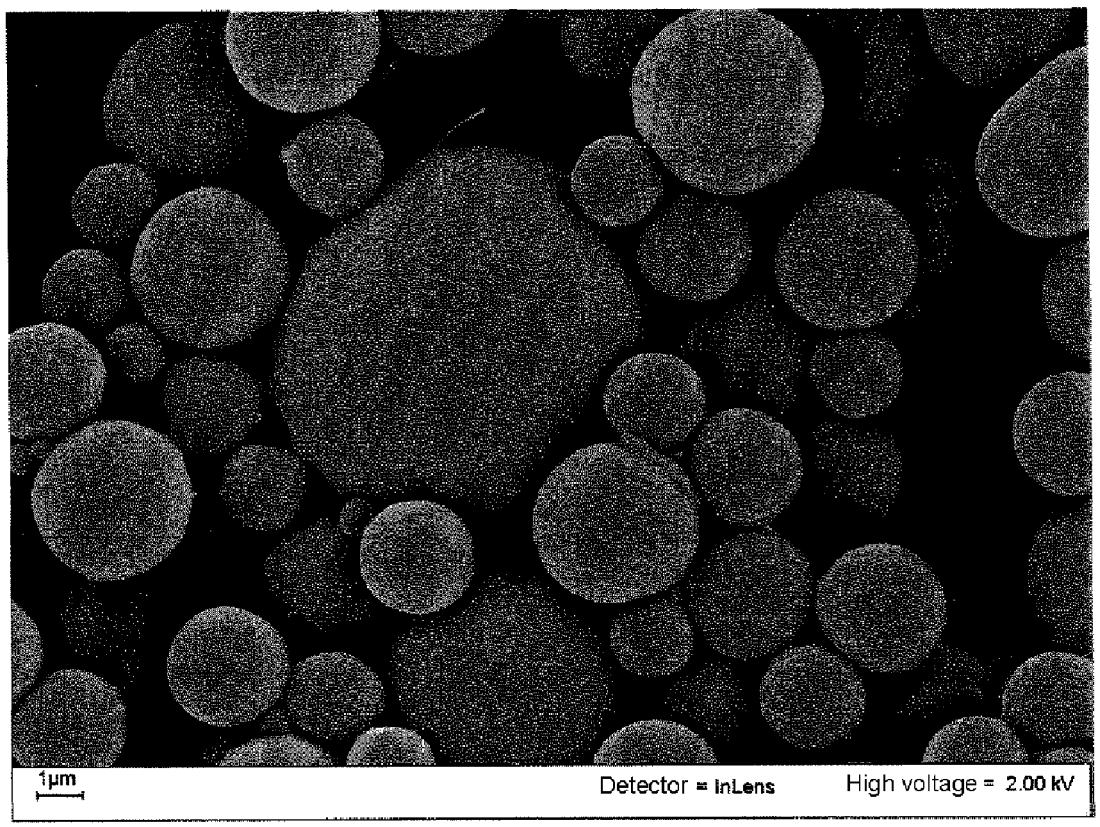

FIG. 4. $S_{16}$ microbeads. The microbeads were obtained by dialysis of a 10 mg/ml $S_{16}$ solution in 6 M GdmSCN against a 1 M potassium phosphate solution pH 7.0 and analyzed by means of scanning electron microscopy.

FIG. 5. Stabilization of $S_{16}$ microbeads. An aqueous 10 mg/ml $S_{16}$ solution was precipitated by adding 1/4 volume of ammonium sulfate at time t=0. At defined time points, portions were removed, a concentration of 4 M urea was established, and extinction at 600 nm was measured as a qualitative measure of scattering and therefore of the presence of stable protein particles.

FIG. 6. $R_{16}$ microbeads with 0.8% β-carotene. The microbeads were obtained by adding a 4 M ammonium sulfate solution to 10 mg/ml $R_{16}$ and 0.08 mg/ml β-carotene in 6 M GdmSCN and analyzed by means of scanning electron microscopy.

Figure 7:
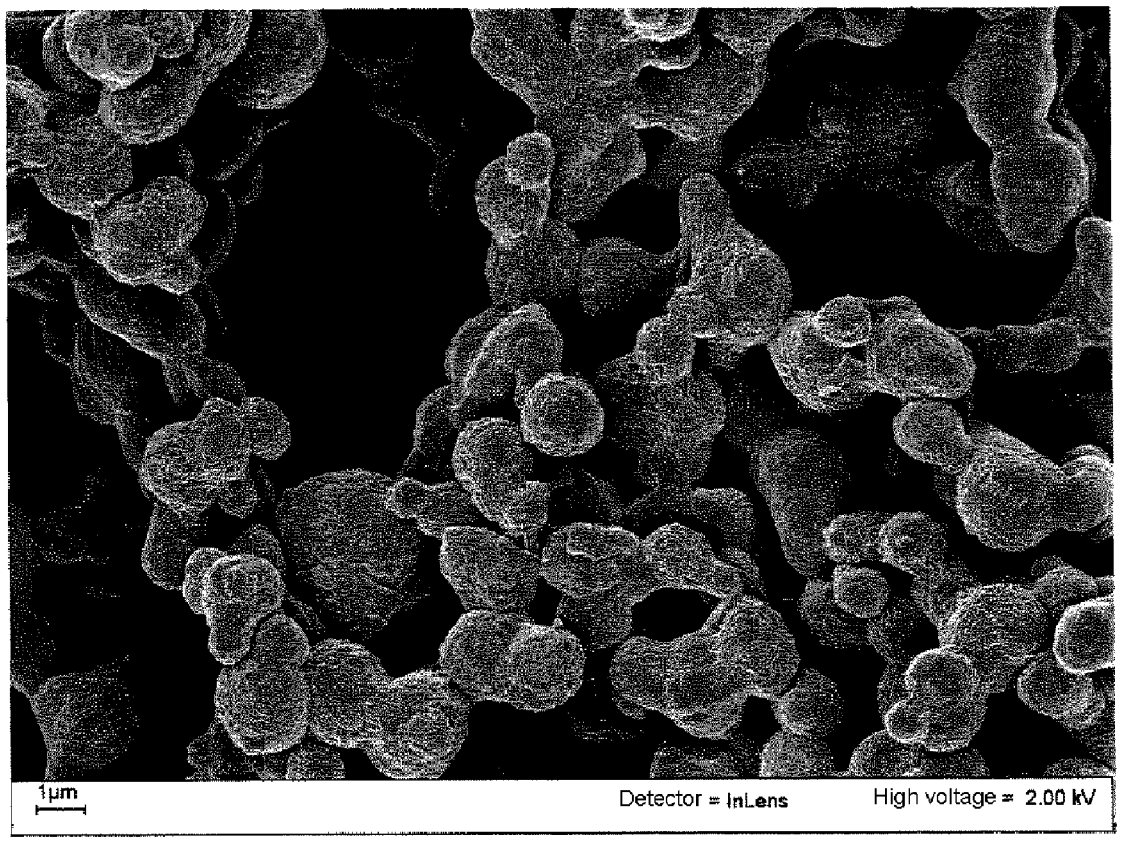

FIG. 7. $S_{16}$ microbeads with 0.8% β-carotene. The microbeads were obtained by adding a 4 M ammonium sulfate solution to 10 mg/ml $S_{16}$ and 0.08 mg/ml β-carotene in 6 M GdmSCN and analyzed by means of scanning electron microscopy.

FIG. 8. Moisture absorption of $R_{16}$ microbeads. The absorption of water was determined by way of the increase in weight of $R_{16}$ microbeads at 100% humidity.

What is claimed is:

1. An isolated repetitive protein wherein at least 80% of the amino acid sequence comprises 10 to 30 repetition units, and wherein said repetition unit comprises either
  the peptide sequence GSSAAAAAAAASG-PGQGQGQGQGQGGRPSDTYG (residues 51-84 of SEQ ID NO:2), or
  the peptide sequence SAAAAAAAAGPGGGNGGRPS-DTYGAPGGGNGGRPSSSYG (residues 95-133 of SEQ ID NO:4).

2. The isolated repetitive protein of claim 1, wherein the peptide sequence of said repetition units consists of the amino acid sequence of SEQ ID NO:2 or SEQ ID NO:4.

3. An isolated nucleic acid sequence coding for the isolated repetitive protein of claim 1.

4. An isolated prokaryotic or eukaryotic host cell comprising the isolated nucleic acid sequence of claim 3.

5. A process for producing the isolated repetitive protein of claim 1, comprising introducing an isolated nucleic acid sequence encoding said protein into an isolated prokaryotic or eukaryotic host cell, inducing the expression of said nucleic acid sequence in the host cell to produce the encoded protein, and subsequently isolating the protein from the host cell.

6. An expression vector comprising the isolated nucleic acid sequence of claim 3.

7. An isolated prokaryotic or eukaryotic host cell comprising the expression vector of claim 6.

* * * * *

SEQUENCE LISTING

```
<160> NUMBER OF SEQ ID NOS: 10

<210> SEQ ID NO 1
<211> LENGTH: 1680
<212> TYPE: DNA
<213> ORGANISM: Artificial Sequence
<220> FEATURE:
<221> NAME/KEY: CDS
<222> LOCATION: (1)..(1680)
<223> OTHER INFORMATION: Synthetic gene coding for repetitive protein
      R16

<400> SEQUENCE: 1 atg gct agc atg act ggt gga cag caa atg ggt cgc gga tcc atg ggc      48
Met Ala Ser Met Thr Gly Gly Gln Gln Met Gly Arg Gly Ser Met Gly
1               5                   10                  15 ccg ggt tct agc gcg gct gca gcc gcg gca gct gcg tcc ggc ccg ggt      96
Pro Gly Ser Ser Ala Ala Ala Ala Ala Ala Ala Ser Gly Pro Gly
            20                  25                  30 cag ggc cag ggt cag ggt caa ggc cag ggt ggc cgt cct tct gac acc      144
Gln Gly Gln Gly Gln Gly Gln Gly Gln Gly Gly Arg Pro Ser Asp Thr
        35                  40                  45 tac ggc ccg ggt tct agc gcg gct gca gcc gcg gca gct gcg tcc ggc      192
Tyr Gly Pro Gly Ser Ser Ala Ala Ala Ala Ala Ala Ala Ser Gly
    50                  55                  60 ccg ggt cag ggc cag ggt cag ggt caa ggc cag ggt ggc cgt cct tct      240
Pro Gly Gln Gly Gln Gly Gln Gly Gln Gly Gln Gly Gly Arg Pro Ser
65                  70                  75                  80 gac acc tac ggc ccg ggt tct agc gcg gct gca gcc gcg gca gct gcg      288
Asp Thr Tyr Gly Pro Gly Ser Ser Ala Ala Ala Ala Ala Ala Ala
                85                  90                  95 tcc ggc ccg ggt cag ggc cag ggt cag ggt caa ggc cag ggt ggc cgt      336
Ser Gly Pro Gly Gln Gly Gln Gly Gln Gly Gln Gly Gln Gly Gly Arg
            100                 105                 110 cct tct gac acc tac ggc ccg ggt tct agc gcg gct gca gcc gcg gca      384
Pro Ser Asp Thr Tyr Gly Pro Gly Ser Ser Ala Ala Ala Ala Ala Ala
        115                 120                 125 gct gcg tcc ggc ccg ggt cag ggc cag ggt cag ggt caa ggc cag ggt      432
Ala Ala Ser Gly Pro Gly Gln Gly Gln Gly Gln Gly Gln Gly Gln Gly
    130                 135                 140 ggc cgt cct tct gac acc tac ggc ccg ggt tct agc gcg gct gca gcc      480
Gly Arg Pro Ser Asp Thr Tyr Gly Pro Gly Ser Ser Ala Ala Ala Ala
145                 150                 155                 160 gcg gca gct gcg tcc ggc ccg ggt cag ggc cag ggt cag ggt caa ggc      528
Ala Ala Ala Ala Ser Gly Pro Gly Gln Gly Gln Gly Gln Gly Gln Gly
                165                 170                 175 cag ggt ggc cgt cct tct gac acc tac ggc ccg ggt tct agc gcg gct      576
Gln Gly Gly Arg Pro Ser Asp Thr Tyr Gly Pro Gly Ser Ser Ala Ala
            180                 185                 190 gca gcc gcg gca gct gcg tcc ggc ccg ggt cag ggc cag ggt cag ggt      624
Ala Ala Ala Ala Ala Ala Ser Gly Pro Gly Gln Gly Gln Gly Gln Gly
        195                 200                 205
```

-continued

```
caa ggc cag ggt ggc cgt cct tct gac acc tac ggc ccg ggt tct agc    672
Gln Gly Gln Gly Gly Arg Pro Ser Asp Thr Tyr Gly Pro Gly Ser Ser
    210             215                 220 gcg gct gca gcc gcg gca gct gcg tcc ggc ccg ggt cag ggc cag ggt    720
Ala Ala Ala Ala Ala Ala Ala Ala Ser Gly Pro Gly Gln Gly Gln Gly
225             230                 235                 240 cag ggt caa ggc cag ggt ggc cgt cct tct gac acc tac ggc ccg ggt    768
Gln Gly Gln Gly Gln Gly Gly Arg Pro Ser Asp Thr Tyr Gly Pro Gly
                245                 250                 255 tct agc gcg gct gca gcc gcg gca gct gcg tcc ggc ccg ggt cag ggc    816
Ser Ser Ala Ala Ala Ala Ala Ala Ala Ser Gly Pro Gly Gln Gly
            260                 265                 270 cag ggt cag ggt caa ggc cag ggt ggc cgt cct tct gac acc tac ggc    864
Gln Gly Gln Gly Gln Gly Gln Gly Gly Arg Pro Ser Asp Thr Tyr Gly
        275                 280                 285 ccg ggt tct agc gcg gct gca gcc gcg gca gct gcg tcc ggc ccg ggt    912
Pro Gly Ser Ser Ala Ala Ala Ala Ala Ala Ala Ser Gly Pro Gly
    290                 295                 300 cag ggc cag ggt cag ggt caa ggc cag ggt ggc cgt cct tct gac acc    960
Gln Gly Gln Gly Gln Gly Gln Gly Gln Gly Gly Arg Pro Ser Asp Thr
305                 310                 315                 320 tac ggc ccg ggt tct agc gcg gct gca gcc gcg gca gct gcg tcc ggc   1008
Tyr Gly Pro Gly Ser Ser Ala Ala Ala Ala Ala Ala Ala Ser Gly
                325                 330                 335 ccg ggt cag ggc cag ggt cag ggt caa ggc cag ggt ggc cgt cct tct   1056
Pro Gly Gln Gly Gln Gly Gln Gly Gln Gly Gln Gly Gly Arg Pro Ser
            340                 345                 350 gac acc tac ggc ccg ggt tct agc gcg gct gca gcc gcg gca gct gcg   1104
Asp Thr Tyr Gly Pro Gly Ser Ser Ala Ala Ala Ala Ala Ala Ala
        355                 360                 365 tcc ggc ccg ggt cag ggc cag ggt cag ggt caa ggc cag ggt ggc cgt   1152
Ser Gly Pro Gly Gln Gly Gln Gly Gln Gly Gln Gly Gln Gly Gly Arg
    370                 375                 380 cct tct gac acc tac ggc ccg ggt tct agc gcg gct gca gcc gcg gca   1200
Pro Ser Asp Thr Tyr Gly Pro Gly Ser Ser Ala Ala Ala Ala Ala
385                 390                 395                 400 gct gcg tcc ggc ccg ggt cag ggc cag ggt cag ggt caa ggc cag ggt   1248
Ala Ala Ser Gly Pro Gly Gln Gly Gln Gly Gln Gly Gln Gly Gln Gly
                405                 410                 415 ggc cgt cct tct gac acc tac ggc ccg ggt tct agc gcg gct gca gcc   1296
Gly Arg Pro Ser Asp Thr Tyr Gly Pro Gly Ser Ser Ala Ala Ala Ala
            420                 425                 430 gcg gca gct gcg tcc ggc ccg ggt cag ggc cag ggt cag ggt caa ggc   1344
Ala Ala Ala Ala Ser Gly Pro Gly Gln Gly Gln Gly Gln Gly Gln Gly
        435                 440                 445 cag ggt ggc cgt cct tct gac acc tac ggc ccg ggt tct agc gcg gct   1392
Gln Gly Gly Arg Pro Ser Asp Thr Tyr Gly Pro Gly Ser Ser Ala Ala
    450                 455                 460 gca gcc gcg gca gct gcg tcc ggc ccg ggt cag ggc cag ggt cag ggt   1440
Ala Ala Ala Ala Ala Ala Ser Gly Pro Gly Gln Gly Gln Gly Gln Gly
465                 470                 475                 480 caa ggc cag ggt ggc cgt cct tct gac acc tac ggc ccg ggt tct agc   1488
Gln Gly Gln Gly Gly Arg Pro Ser Asp Thr Tyr Gly Pro Gly Ser Ser
                485                 490                 495 gcg gct gca gcc gcg gca gct gcg tcc ggc ccg ggt cag ggc cag ggt   1536
Ala Ala Ala Ala Ala Ala Ala Ser Gly Pro Gly Gln Gly Gln Gly
            500                 505                 510 cag ggt caa ggc cag ggt ggc cgt cct tct gac acc tac ggc ccg ggt   1584
Gln Gly Gln Gly Gln Gly Gly Arg Pro Ser Asp Thr Tyr Gly Pro Gly
        515                 520                 525
```

-continued

```
tct agc gcg gct gca gcc gcg gca gct gcg tcc ggc ccg ggt cag ggc    1632
Ser Ser Ala Ala Ala Ala Ala Ala Ala Ala Ser Gly Pro Gly Gln Gly
530                 535                 540 cag ggt cag ggt caa ggc cag ggt ggc cgt cct tct gac acc tac ggc    1680
Gln Gly Gln Gly Gln Gly Gln Gly Gly Arg Pro Ser Asp Thr Tyr Gly
545                 550                 555                 560

<210> SEQ ID NO 2
<211> LENGTH: 560
<212> TYPE: PRT
<213> ORGANISM: Artificial Sequence
<220> FEATURE:
<223> OTHER INFORMATION: Repetitive protein R16

<400> SEQUENCE: 2

Met Ala Ser Met Thr Gly Gly Gln Gln Met Gly Arg Gly Ser Met Gly
1               5                   10                  15

Pro Gly Ser Ser Ala Ala Ala Ala Ala Ala Ala Ser Gly Pro Gly
            20                  25                  30

Gln Gly Gln Gly Gln Gly Gln Gly Gln Gly Gly Arg Pro Ser Asp Thr
                35                  40                  45

Tyr Gly Pro Gly Ser Ser Ala Ala Ala Ala Ala Ala Ala Ser Gly
50                  55                  60

Pro Gly Gln Gly Gln Gly Gln Gly Gln Gly Gln Gly Gly Arg Pro Ser
65                  70                  75                  80

Asp Thr Tyr Gly Pro Gly Ser Ser Ala Ala Ala Ala Ala Ala Ala Ala
                85                  90                  95

Ser Gly Pro Gly Gln Gly Gln Gly Gln Gly Gln Gly Gln Gly Gly Arg
                100                 105                 110

Pro Ser Asp Thr Tyr Gly Pro Gly Ser Ser Ala Ala Ala Ala Ala
                115                 120                 125

Ala Ala Ser Gly Pro Gly Gln Gly Gln Gly Gln Gly Gln Gly Gln Gly
            130                 135                 140

Gly Arg Pro Ser Asp Thr Tyr Gly Pro Gly Ser Ser Ala Ala Ala Ala
145                 150                 155                 160

Ala Ala Ala Ala Ser Gly Pro Gly Gln Gly Gln Gly Gln Gly Gln Gly
                165                 170                 175

Gln Gly Gly Arg Pro Ser Asp Thr Tyr Gly Pro Gly Ser Ser Ala Ala
                180                 185                 190

Ala Ala Ala Ala Ala Ser Gly Pro Gly Gln Gly Gln Gly Gln Gly
            195                 200                 205

Gln Gly Gln Gly Gly Arg Pro Ser Asp Thr Tyr Gly Pro Gly Ser Ser
210                 215                 220

Ala Ala Ala Ala Ala Ala Ala Ser Gly Pro Gly Gln Gly Gln Gly
225                 230                 235                 240

Gln Gly Gln Gly Gln Gly Gly Arg Pro Ser Asp Thr Tyr Gly Pro Gly
                245                 250                 255

Ser Ser Ala Ala Ala Ala Ala Ala Ala Ser Gly Pro Gly Gln Gly
            260                 265                 270

Gln Gly Gln Gly Gln Gly Gln Gly Gly Arg Pro Ser Asp Thr Tyr Gly
            275                 280                 285

Pro Gly Ser Ser Ala Ala Ala Ala Ala Ala Ala Ser Gly Pro Gly
            290                 295                 300

Gln Gly Gln Gly Gln Gly Gln Gly Gly Arg Pro Ser Asp Thr
305                 310                 315                 320

Tyr Gly Pro Gly Ser Ser Ala Ala Ala Ala Ala Ala Ala Ala Ser Gly
```

```
                       325                 330                 335
Pro Gly Gln Gly Gln Gly Gln Gly Gln Gly Gly Arg Pro Ser
            340                 345                 350
Asp Thr Tyr Gly Pro Gly Ser Ser Ala Ala Ala Ala Ala Ala
            355                 360                 365
Ser Gly Pro Gly Gln Gly Gln Gly Gln Gly Gln Gly Gly Arg
            370                 375                 380
Pro Ser Asp Thr Tyr Gly Pro Gly Ser Ser Ala Ala Ala Ala
385                 390                 395                 400
Ala Ala Ser Gly Pro Gly Gln Gly Gln Gly Gln Gly Gln Gly
                405                 410                 415
Gly Arg Pro Ser Asp Thr Tyr Gly Pro Gly Ser Ser Ala Ala Ala
                420                 425                 430
Ala Ala Ala Ala Ser Gly Pro Gly Gln Gly Gln Gly Gln Gly
                435                 440                 445
Gln Gly Gly Arg Pro Ser Asp Thr Tyr Gly Pro Gly Ser Ser Ala Ala
            450                 455                 460
Ala Ala Ala Ala Ala Ser Gly Pro Gly Gln Gly Gln Gly Gln Gly
465                 470                 475                 480
Gln Gly Gln Gly Gly Arg Pro Ser Asp Thr Tyr Gly Pro Gly Ser Ser
                485                 490                 495
Ala Ala Ala Ala Ala Ala Ser Gly Pro Gly Gln Gly Gln Gly
                500                 505                 510
Gln Gly Gln Gly Gly Arg Pro Ser Asp Thr Tyr Gly Pro Gly
                515                 520                 525
Ser Ser Ala Ala Ala Ala Ala Ala Ser Gly Pro Gly Gln Gly
            530                 535                 540
Gln Gly Gln Gly Gln Gly Gly Arg Pro Ser Asp Thr Tyr Gly
545                 550                 555                 560

<210> SEQ ID NO 3
<211> LENGTH: 1920
<212> TYPE: DNA
<213> ORGANISM: Artificial Sequence
<220> FEATURE:
<221> NAME/KEY: CDS
<222> LOCATION: (1)..(1920)
<223> OTHER INFORMATION: Synthetic gene coding for repetitive protein
      S16

<400> SEQUENCE: 3 atg gct agc atg act ggt gga cag caa atg ggt cgc gga tcc atg ggt        48
Met Ala Ser Met Thr Gly Gly Gln Gln Met Gly Arg Gly Ser Met Gly
1               5                   10                  15 tct gcg gct gca gcc gcg gca gct gcg ggt ccg ggc ggt ggc aac ggt        96
Ser Ala Ala Ala Ala Ala Ala Ala Ala Gly Pro Gly Gly Gly Asn Gly
                20                  25                  30 ggc cgt ccg tct gac acc tac ggt gcg ccg ggt ggc ggt aac ggt ggc       144
Gly Arg Pro Ser Asp Thr Tyr Gly Ala Pro Gly Gly Gly Asn Gly Gly
            35                  40                  45 cgt cct tct tcc tct tac ggt tct gcg gct gca gcc gcg gca gct gcg       192
Arg Pro Ser Ser Ser Tyr Gly Ser Ala Ala Ala Ala Ala Ala Ala Ala
        50                  55                  60 ggt ccg ggc ggt ggc aac ggt ggc cgt ccg tct gac acc tac ggt gcg       240
Gly Pro Gly Gly Gly Asn Gly Gly Arg Pro Ser Asp Thr Tyr Gly Ala
65                  70                  75                  80 ccg ggt ggc ggt aac ggt ggc cgt cct tct tcc tct tac ggt tct gcg       288
Pro Gly Gly Gly Asn Gly Gly Arg Pro Ser Ser Ser Tyr Gly Ser Ala
                85                  90                  95
```

```
gct gca gcc gcg gca gct gcg ggt ccg ggc ggt ggc aac ggt ggc cgt    336
Ala Ala Ala Ala Ala Ala Ala Gly Pro Gly Gly Gly Asn Gly Gly Arg
        100                 105                 110 ccg tct gac acc tac ggt gcg ccg ggt ggc ggt aac ggt ggc cgt cct    384
Pro Ser Asp Thr Tyr Gly Ala Pro Gly Gly Gly Asn Gly Gly Arg Pro
        115                 120                 125 tct tcc tct tac ggt tct gcg gct gca gcc gcg gca gct gcg ggt ccg    432
Ser Ser Ser Tyr Gly Ser Ala Ala Ala Ala Ala Ala Ala Ala Gly Pro
        130                 135                 140 ggc ggt ggc aac ggt ggc cgt ccg tct gac acc tac ggt gcg ccg ggt    480
Gly Gly Gly Asn Gly Gly Arg Pro Ser Asp Thr Tyr Gly Ala Pro Gly
145                 150                 155                 160 ggc ggt aac ggt ggc cgt cct tct tcc tct tac ggt tct gcg gct gca    528
Gly Gly Asn Gly Gly Arg Pro Ser Ser Ser Tyr Gly Ser Ala Ala Ala
                165                 170                 175 gcc gcg gca gct gcg ggt ccg ggc ggt ggc aac ggt ggc cgt ccg tct    576
Ala Ala Ala Ala Ala Gly Pro Gly Gly Gly Asn Gly Gly Arg Pro Ser
            180                 185                 190 gac acc tac ggt gcg ccg ggt ggc ggt aac ggt ggc cgt cct tct tcc    624
Asp Thr Tyr Gly Ala Pro Gly Gly Gly Asn Gly Gly Arg Pro Ser Ser
        195                 200                 205 tct tac ggt tct gcg gct gca gcc gcg gca gct gcg ggt ccg ggc ggt    672
Ser Tyr Gly Ser Ala Ala Ala Ala Ala Ala Ala Ala Gly Pro Gly Gly
        210                 215                 220 ggc aac ggt ggc cgt ccg tct gac acc tac ggt gcg ccg ggt ggc ggt    720
Gly Asn Gly Gly Arg Pro Ser Asp Thr Tyr Gly Ala Pro Gly Gly Gly
225                 230                 235                 240 aac ggt ggc cgt cct tct tcc tct tac ggt tct gcg gct gca gcc gcg    768
Asn Gly Gly Arg Pro Ser Ser Ser Tyr Gly Ser Ala Ala Ala Ala Ala
                245                 250                 255 gca gct gcg ggt ccg ggc ggt ggc aac ggt ggc cgt ccg tct gac acc    816
Ala Ala Ala Gly Pro Gly Gly Gly Asn Gly Gly Arg Pro Ser Asp Thr
            260                 265                 270 tac ggt gcg ccg ggt ggc ggt aac ggt ggc cgt cct tct tcc tct tac    864
Tyr Gly Ala Pro Gly Gly Gly Asn Gly Gly Arg Pro Ser Ser Ser Tyr
        275                 280                 285 ggt tct gcg gct gca gcc gcg gca gct gcg ggt ccg ggc ggt ggc aac    912
Gly Ser Ala Ala Ala Ala Ala Ala Ala Ala Gly Pro Gly Gly Gly Asn
        290                 295                 300 ggt ggc cgt ccg tct gac acc tac ggt gcg ccg ggt ggc ggt aac ggt    960
Gly Gly Arg Pro Ser Asp Thr Tyr Gly Ala Pro Gly Gly Gly Asn Gly
305                 310                 315                 320 ggc cgt cct tct tcc tct tac ggt tct gcg gct gca gcc gcg gca gct    1008
Gly Arg Pro Ser Ser Ser Tyr Gly Ser Ala Ala Ala Ala Ala Ala Ala
                325                 330                 335 gcg ggt ccg ggc ggt ggc aac ggt ggc cgt ccg tct gac acc tac ggt    1056
Ala Gly Pro Gly Gly Gly Asn Gly Gly Arg Pro Ser Asp Thr Tyr Gly
            340                 345                 350 gcg ccg ggt ggc ggt aac ggt ggc cgt cct tct tcc tct tac ggt tct    1104
Ala Pro Gly Gly Gly Asn Gly Gly Arg Pro Ser Ser Ser Tyr Gly Ser
        355                 360                 365 gcg gct gca gcc gcg gca gct gcg ggt ccg ggc ggt ggc aac ggt ggc    1152
Ala Ala Ala Ala Ala Ala Ala Ala Gly Pro Gly Gly Gly Asn Gly Gly
        370                 375                 380 cgt ccg tct gac acc tac ggt gcg ccg ggt ggc ggt aac ggt ggc cgt    1200
Arg Pro Ser Asp Thr Tyr Gly Ala Pro Gly Gly Gly Asn Gly Gly Arg
385                 390                 395                 400 cct tct tcc tct tac ggt tct gcg gct gca gcc gcg gca gct gcg ggt    1248
Pro Ser Ser Ser Tyr Gly Ser Ala Ala Ala Ala Ala Ala Ala Ala Gly
                405                 410                 415
```

```
ccg ggc ggt ggc aac ggt ggc cgt ccg tct gac acc tac ggt gcg ccg       1296
Pro Gly Gly Gly Asn Gly Gly Arg Pro Ser Asp Thr Tyr Gly Ala Pro
            420                 425                 430 ggt ggc ggt aac ggt ggc cgt cct tct tcc tct tac ggt tct gcg gct       1344
Gly Gly Gly Asn Gly Gly Arg Pro Ser Ser Ser Tyr Gly Ser Ala Ala
            435                 440                 445 gca gcc gcg gca gct gcg ggt ccg ggt ggc aac ggt ggc cgt ccg           1392
Ala Ala Ala Ala Ala Ala Gly Pro Gly Gly Gly Asn Gly Gly Arg Pro
    450                 455                 460 tct gac acc tac ggt gcg ccg ggt ggc ggt aac ggt ggc cgt cct tct       1440
Ser Asp Thr Tyr Gly Ala Pro Gly Gly Gly Asn Gly Gly Arg Pro Ser
465                 470                 475                 480 tcc tct tac ggt tct gcg gct gca gcc gcg gca gct gcg ggt ccg ggc       1488
Ser Ser Tyr Gly Ser Ala Ala Ala Ala Ala Ala Ala Ala Gly Pro Gly
                485                 490                 495 ggt ggc aac ggt ggc cgt ccg tct gac acc tac ggt gcg ccg ggt ggc       1536
Gly Gly Asn Gly Gly Arg Pro Ser Asp Thr Tyr Gly Ala Pro Gly Gly
            500                 505                 510 ggt aac ggt ggc cgt cct tct tcc tct tac ggt tct gcg gct gca gcc       1584
Gly Asn Gly Gly Arg Pro Ser Ser Ser Tyr Gly Ser Ala Ala Ala Ala
            515                 520                 525 gcg gca gct gcg ggt ccg ggc ggt ggc aac ggt ggc cgt ccg tct gac       1632
Ala Ala Ala Ala Gly Pro Gly Gly Gly Asn Gly Gly Arg Pro Ser Asp
    530                 535                 540 acc tac ggt gcg ccg ggt ggc ggt aac ggt ggc cgt cct tct tcc tct       1680
Thr Tyr Gly Ala Pro Gly Gly Gly Asn Gly Gly Arg Pro Ser Ser Ser
545                 550                 555                 560 tac ggt tct gcg gct gca gcc gcg gca gct gcg ggt ccg ggc ggt ggc       1728
Tyr Gly Ser Ala Ala Ala Ala Ala Ala Ala Ala Gly Pro Gly Gly Gly
                565                 570                 575 aac ggt ggc cgt ccg tct gac acc tac ggt gcg ccg ggt ggc ggt aac       1776
Asn Gly Gly Arg Pro Ser Asp Thr Tyr Gly Ala Pro Gly Gly Gly Asn
            580                 585                 590 ggt ggc cgt cct tct tcc tct tac ggt tct gcg gct gca gcc gcg gca       1824
Gly Gly Arg Pro Ser Ser Ser Tyr Gly Ser Ala Ala Ala Ala Ala Ala
            595                 600                 605 gct gcg ggt ccg ggc ggt ggc aac ggt ggc cgt ccg tct gac acc tac       1872
Ala Ala Gly Pro Gly Gly Gly Asn Gly Gly Arg Pro Ser Asp Thr Tyr
    610                 615                 620 ggt gcg ccg ggt ggc ggt aac ggt ggc cgt cct tct tcc tct tac ggc       1920
Gly Ala Pro Gly Gly Gly Asn Gly Gly Arg Pro Ser Ser Ser Tyr Gly
625                 630                 635                 640

<210> SEQ ID NO 4
<211> LENGTH: 640
<212> TYPE: PRT
<213> ORGANISM: Artificial Sequence
<220> FEATURE:
<223> OTHER INFORMATION: Repetitive protein S16

<400> SEQUENCE: 4

Met Ala Ser Met Thr Gly Gly Gln Gln Met Gly Arg Gly Ser Met Gly
1               5                   10                  15

Ser Ala Ala Ala Ala Ala Ala Ala Gly Pro Gly Gly Gly Asn Gly
            20                  25                  30

Gly Arg Pro Ser Asp Thr Tyr Gly Ala Pro Gly Gly Gly Asn Gly Gly
            35                  40                  45

Arg Pro Ser Ser Ser Tyr Gly Ser Ala Ala Ala Ala Ala Ala Ala Ala
        50                  55                  60

Gly Pro Gly Gly Gly Asn Gly Gly Arg Pro Ser Asp Thr Tyr Gly Ala
```

```
                65                  70                  75                  80
Pro Gly Gly Gly Asn Gly Gly Arg Pro Ser Ser Tyr Gly Ser Ala
                    85                  90                  95
Ala Ala Ala Ala Ala Ala Ala Gly Pro Gly Gly Gly Asn Gly Arg
                100                 105                 110
Pro Ser Asp Thr Tyr Gly Ala Pro Gly Gly Gly Asn Gly Arg Pro
                115                 120                 125
Ser Ser Ser Tyr Gly Ser Ala Ala Ala Ala Ala Ala Ala Gly Pro
                130                 135                 140
Gly Gly Gly Asn Gly Gly Arg Pro Ser Asp Thr Tyr Gly Ala Pro Gly
145                 150                 155                 160
Gly Gly Asn Gly Gly Arg Pro Ser Ser Tyr Gly Ser Ala Ala Ala
                165                 170                 175
Ala Ala Ala Ala Ala Gly Pro Gly Gly Gly Asn Gly Gly Arg Pro Ser
                180                 185                 190
Asp Thr Tyr Gly Ala Pro Gly Gly Gly Asn Gly Gly Arg Pro Ser Ser
                195                 200                 205
Ser Tyr Gly Ser Ala Ala Ala Ala Ala Ala Ala Gly Pro Gly Gly
    210                 215                 220
Gly Asn Gly Gly Arg Pro Ser Asp Thr Tyr Gly Ala Pro Gly Gly Gly
225                 230                 235                 240
Asn Gly Gly Arg Pro Ser Ser Ser Tyr Gly Ser Ala Ala Ala Ala
                    245                 250                 255
Ala Ala Ala Gly Pro Gly Gly Gly Asn Gly Gly Arg Pro Ser Asp Thr
            260                 265                 270
Tyr Gly Ala Pro Gly Gly Gly Asn Gly Gly Arg Pro Ser Ser Ser Tyr
        275                 280                 285
Gly Ser Ala Ala Ala Ala Ala Ala Ala Gly Pro Gly Gly Gly Asn
    290                 295                 300
Gly Gly Arg Pro Ser Asp Thr Tyr Gly Ala Pro Gly Gly Gly Asn Gly
305                 310                 315                 320
Gly Arg Pro Ser Ser Ser Tyr Gly Ser Ala Ala Ala Ala Ala Ala
                325                 330                 335
Ala Gly Pro Gly Gly Gly Asn Gly Gly Arg Pro Ser Asp Thr Tyr Gly
        340                 345                 350
Ala Pro Gly Gly Gly Asn Gly Gly Arg Pro Ser Ser Ser Tyr Gly Ser
            355                 360                 365
Ala Ala Ala Ala Ala Ala Ala Gly Pro Gly Gly Gly Asn Gly Gly
    370                 375                 380
Arg Pro Ser Asp Thr Tyr Gly Ala Pro Gly Gly Gly Asn Gly Gly Arg
385                 390                 395                 400
Pro Ser Ser Ser Tyr Gly Ser Ala Ala Ala Ala Ala Ala Ala Gly
                405                 410                 415
Pro Gly Gly Gly Asn Gly Gly Arg Pro Ser Asp Thr Tyr Gly Ala Pro
            420                 425                 430
Gly Gly Gly Asn Gly Gly Arg Pro Ser Ser Ser Tyr Gly Ser Ala Ala
            435                 440                 445
Ala Ala Ala Ala Ala Gly Pro Gly Gly Gly Asn Gly Gly Arg Pro
    450                 455                 460
Ser Asp Thr Tyr Gly Ala Pro Gly Gly Gly Asn Gly Gly Arg Pro Ser
465                 470                 475                 480
Ser Ser Tyr Gly Ser Ala Ala Ala Ala Ala Ala Ala Gly Pro Gly
                485                 490                 495
```

```
Gly Gly Asn Gly Gly Arg Pro Ser Asp Thr Tyr Gly Ala Pro Gly Gly
                500                 505                 510
Gly Asn Gly Gly Arg Pro Ser Ser Tyr Gly Ser Ala Ala Ala Ala Ala
            515                 520                 525
Ala Ala Ala Gly Pro Gly Gly Asn Gly Gly Arg Pro Ser Asp
        530                 535                 540
Thr Tyr Gly Ala Pro Gly Gly Asn Gly Gly Arg Pro Ser Ser Ser
545                 550                 555                 560
Tyr Gly Ser Ala Ala Ala Ala Ala Ala Gly Pro Gly Gly
            565                 570                 575
Asn Gly Gly Arg Pro Ser Asp Thr Tyr Gly Ala Pro Gly Gly Asn
            580                 585                 590
Gly Gly Arg Pro Ser Ser Ser Tyr Gly Ser Ala Ala Ala Ala Ala
            595                 600                 605
Ala Ala Gly Pro Gly Gly Asn Gly Gly Arg Pro Ser Asp Thr Tyr
        610                 615                 620
Gly Ala Pro Gly Gly Asn Gly Gly Arg Pro Ser Ser Ser Tyr Gly
625                 630                 635                 640

<210> SEQ ID NO 5
<211> LENGTH: 6
<212> TYPE: PRT
<213> ORGANISM: Artificial Sequence
<220> FEATURE:
<223> OTHER INFORMATION: 6 X His tag

<400> SEQUENCE: 5

His His His His His His
1               5

<210> SEQ ID NO 6
<211> LENGTH: 11
<212> TYPE: PRT
<213> ORGANISM: Artificial Sequence
<220> FEATURE:
<223> OTHER INFORMATION: T7 tag

<400> SEQUENCE: 6

Met Ala Ser Met Thr Gly Gly Gln Gln Met Gly
1               5                   10

<210> SEQ ID NO 7
<211> LENGTH: 15
<212> TYPE: PRT
<213> ORGANISM: Artificial Sequence
<220> FEATURE:
<223> OTHER INFORMATION: S tag

<400> SEQUENCE: 7

Lys Glu Thr Ala Ala Ala Lys Phe Glu Arg Gln His Met Asp Ser
1               5                   10                  15

<210> SEQ ID NO 8
<211> LENGTH: 10
<212> TYPE: PRT
<213> ORGANISM: Artificial Sequence
<220> FEATURE:
<223> OTHER INFORMATION: c-Myc tag

<400> SEQUENCE: 8

Glu Gln Lys Leu Ile Ser Glu Glu Asp Leu
1               5                   10
```

```
<210> SEQ ID NO 9
<211> LENGTH: 8
<212> TYPE: PRT
<213> ORGANISM: Artificial Sequence
<220> FEATURE:
<223> OTHER INFORMATION: Strep tag

<400> SEQUENCE: 9

Trp Ser His Pro Gln Phe Glu Lys
1               5

<210> SEQ ID NO 10
<211> LENGTH: 9
<212> TYPE: PRT
<213> ORGANISM: Artificial Sequence
<220> FEATURE:
<223> OTHER INFORMATION: HA tag

<400> SEQUENCE: 10

Tyr Pro Tyr Asp Val Pro Asp Tyr Ala
1               5
```